(12) United States Patent
Jamiolkowski et al.

(10) Patent No.: US 8,197,837 B2
(45) Date of Patent: Jun. 12, 2012

(54) METHOD OF PREPARATION OF BIOABSORBABLE POROUS REINFORCED TISSUE IMPLANTS AND IMPLANTS THEREOF

(75) Inventors: Dennis D. Jamiolkowski, Long Valley, NJ (US); Kelly R. Brown, Flanders, NJ (US); Iksoo Chun, Princeton, NJ (US); Mora Carolynne Melican, Upper Montclair, NJ (US)

(73) Assignee: DePuy Mitek, Inc., Raynham, MA (US)

( * ) Notice: Subject to any disclaimer, the term of this patent is extended or adjusted under 35 U.S.C. 154(b) by 1851 days.

(21) Appl. No.: 10/955,370

(22) Filed: Sep. 30, 2004

(65) Prior Publication Data

US 2005/0113938 A1 May 26, 2005

(51) Int. Cl.
*A61F 13/00* (2006.01)

(52) U.S. Cl. ........................................ 424/422; 424/423

(58) Field of Classification Search .................. 424/422, 424/423
See application file for complete search history.

(56) References Cited

U.S. PATENT DOCUMENTS

| | | | |
|---|---|---|---|
| 5,108,807 A | 4/1992 | Tucker |
| 5,290,494 A | 3/1994 | Coombes |
| 5,320,624 A | 6/1994 | Kaplan |
| 5,626,611 A | 5/1997 | Liu |
| 5,782,914 A | 7/1998 | Schankereli |
| 5,837,278 A | 11/1998 | Geistlich |
| 6,147,135 A | 11/2000 | Yuan |
| 6,171,338 B1 | 1/2001 | Talja |
| 6,287,316 B1 | 9/2001 | Agarwal |
| 6,503,278 B1 | 1/2003 | Pohjonen |
| 6,511,511 B1 | 1/2003 | Kieswetter et al. |
| 6,599,323 B2 | 7/2003 | Melican |
| 6,852,330 B2 | 2/2005 | Bowman |
| 2001/0033857 A1 | 10/2001 | Vyakarnam |
| 2004/0175408 A1 | 9/2004 | Chun et al. |
| 2008/0241213 A1 | 10/2008 | Chun |

FOREIGN PATENT DOCUMENTS

| | | |
|---|---|---|
| EP | 0 274 898 | 7/1988 |
| EP | 1 216 717 | 6/2002 |
| JP | 04502715 | 5/1992 |
| JP | 11512626 | 11/1999 |

OTHER PUBLICATIONS

EP Search Report for EP Appln. No. EP 05 25 6123 dated Feb. 1, 2006.
EPO Search Rerport dated Jul. 9, 2004 for EPO Application No. 04251265.7.
Handbook of Fiber Science and Technology, Edited by Menachem Lewin, Jack Preston, vol. III, Part B, Chapter 8, by Yoshito Ikada, pp. 253, 259-261, Published by M. Dekker, 1983.
Warm Glass Disclosure, "The Basic Fusing and Slumping Process", 1999.
Guy Fortier, Development of Biosensors Based on Immobilization of Enzymes in Eastman AQ Polymer Coated with a Layer of Nafion, Analytical Letters, vol. 23 No. 9, Sep. 1990.

*Primary Examiner* — Michael G Hartley

(57) ABSTRACT

A biocompatible tissue implant. The tissue implant may be bioabsorbable, consists of a biocompatible polymeric foam. The tissue implant also includes a biocompatible reinforcement member. The polymeric foam and the reinforcement member are soluble in a lyophilizing solvent. The reinforcement may be annealed and/or coated.

20 Claims, 12 Drawing Sheets

(a) coating thickness = 1.0 mil

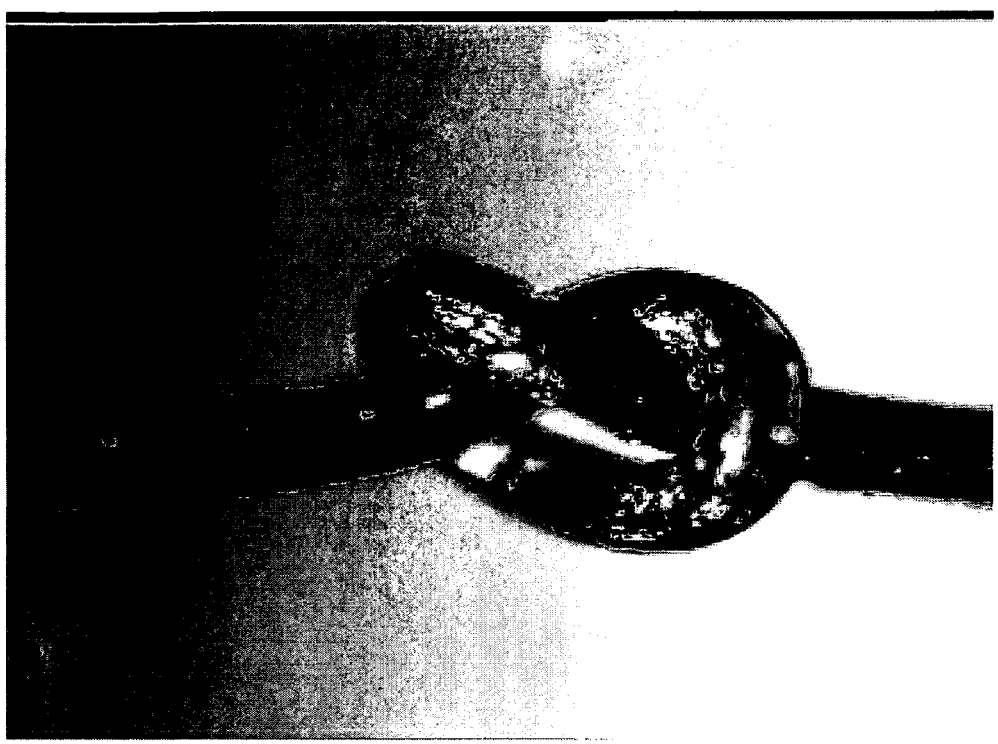
Fig. 10 (b) coating thickness = 1.75 mil

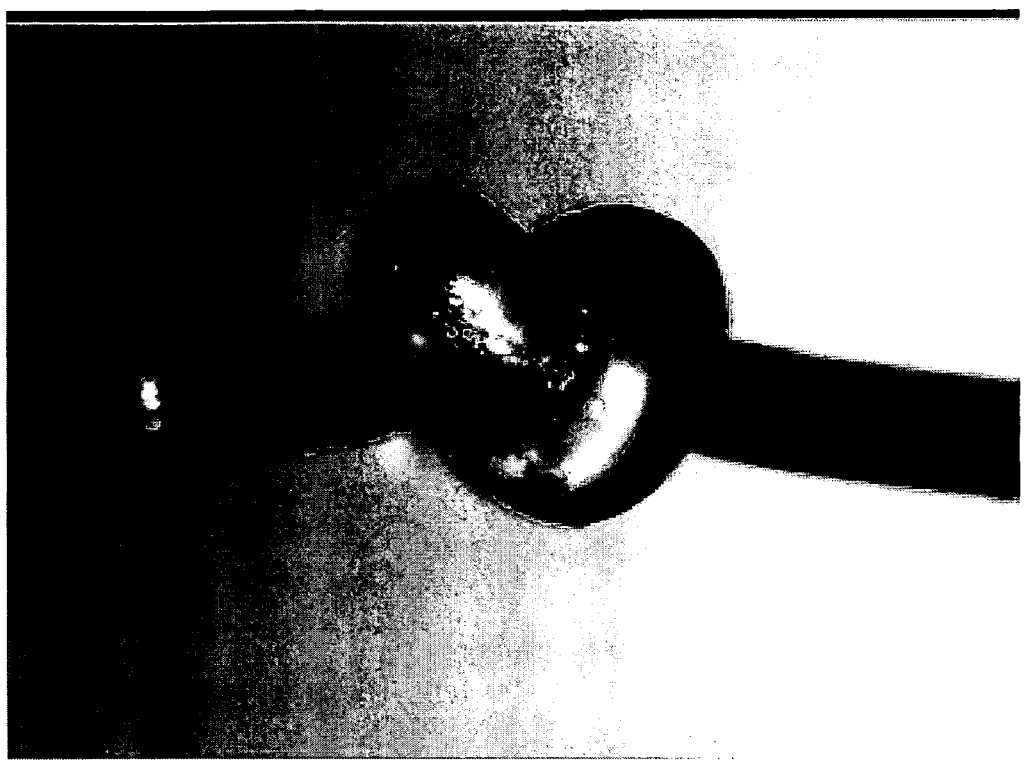
Fig. 10 (c) coating thickness = 2.375 mil

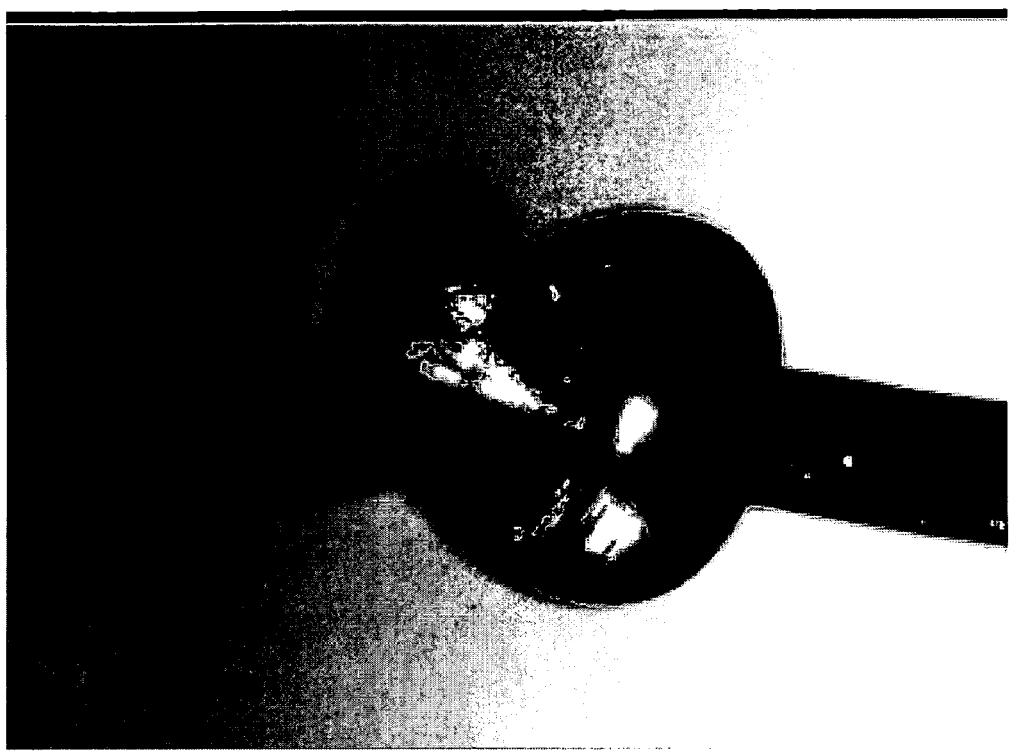
Fig. 10 (d) coating thickness = 4.0 mil

METHOD OF PREPARATION OF BIOABSORBABLE POROUS REINFORCED TISSUE IMPLANTS AND IMPLANTS THEREOF

FIELD OF THE INVENTION

The present invention relates to bioabsorbable, porous, reinforced implantable devices for use in the repair of soft tissue injuries, and methods of using and manufacturing such devices.

BACKGROUND OF THE INVENTION

Injuries to soft tissue, including, for example, musculoskeletal tissue, may require repair by surgical intervention, depending upon factors such as the severity and type of injury. Such surgical repairs can be affected by using a number of conventional surgical procedures, for example, by suturing the damaged tissue, and/or by mounting an implant to the damaged tissue. It is known that an implant may provide structural support to the damaged tissue, and it may also serve as a substrate upon which cells can grow, thus facilitating more rapid healing.

One example of a fairly common tissue injury is damage to or prolapse of the pelvic floor. This is a potentially serious medical condition that may occur during childbirth or from subsequent complications, which can lead to an injury of the vesicovaginal fascia. This type of injury may result in a cystocele, which is a herniation of the bladder. Similar medical conditions include rectoceles (a herniation of the rectum), enteroceles (a protrusion of the intestine through the rectovaginal or vesicovaginal pouch), and enterocystoceles (a double hernia in which both the bladder and intestine protrude).

Another example of a fairly common soft tissue injury is damage to the rotator cuff or rotator cuff tendons. The rotator cuff facilitates circular motion of the humerus relative to the scapula. Damage to the rotator cuff is a potentially serious medical condition that may occur during hyperextension, from an acute traumatic tear or from overuse of the joint. The most common injury associated with the rotator cuff region is a strain or tear involving the supraspinatus tendon. A tear at the insertion site of the tendon with the humerus, may result in the detachment of the tendon from the bone. This detachment may be partial or full, depending upon the severity of the injury. Additionally, the strain or tear can occur within the tendon itself. Treatment for a strained tendon usually involves physical cessation from use of the tendon, i.e., rest. However, depending upon the severity of the injury, a torn tendon might require surgical intervention as in the case of a full tear or detachment of the supraspinatus tendon from the humerus. Damage to the rotator cuff may also include degeneration. This is a common situation that arises in elderly patients. In degenerative cases there is loss of the superior portion of the rotator cuff with complete loss of the supraspinatus tendon. Similar soft tissue pathologies include tears in the Achilles' tendon, the anterior cruciate ligament and other tendons or ligaments of the knee, wrist, hand, and hip, spine, etc.

One example of a common ligament injury is a torn anterior cruciate ligament (ACL), which is one of four major ligaments of the knee. The primary function of the ACL is to constrain anterior translation, rotary laxity and hyperextension. The lack of an ACL causes instability of the knee joint and leads to degenerative changes in the knee such as osteoarthritis. The most common repair technique is to remove and discard the ruptured ACL and reconstruct a new ACL using autologous grafts such as bone-patellar-tendon-bone grafts or hamstring tendon grafts. Although this technique has shown long-term clinical efficacy, there is morbidity associated with the harvest site of the tissue graft. Synthetic prosthetic devices are known and have been clinically evaluated in the past with little long-term success. The advantages of a synthetic implant are that the patient does not suffer from the donor site morbidity that is associated with autograft procedures, and that patients having a synthetic implant are able to undergo faster rehabilitation of the knee. These synthetic prosthetic devices were composed of non-resorbable materials and were designed to be permanent prosthetic implants. A number of disadvantages may be associated with synthetic prosthetic implants, such as for example, synovitis, bone tunnel enlargement, wear debris, and elongation and rupture of the devices. Allografts are also used in ACL reconstructive procedures, however there are disadvantages associated with their use as described in more detail below. Overall, autograft reconstruction is still the widely accepted solution for repairing a ruptured ACL.

Herniation and tears of soft tissue are typically treated by conventional surgical procedures in which the protruding organs or tissue tears are repositioned or reconsolidated. The prevailing standard of care for some procedures, for example, is to use a conventional mesh-like patch to repair the damaged site. There is a constant need in this art for new surgical procedures for the treatment and repair of damaged soft tissue that facilitate more rapid healing and improved patient outcomes. In response to this need, a variety of implants in addition to meshes have been developed and used in surgical procedures to help achieve these benefits. One type of conventional implant is made from biologically derived tissue (e.g. allografts and autografts). Biologically derived materials, although generally safe and effective, may have several disadvantages associated with their use. For example, if not properly aseptically processed in accordance with prevailing and accepted standards and regulations, they may contribute to disease transmission. In addition, biologically derived products may be somewhat difficult to harvest and acquire, and, may be burdensome to process such that their properties are within required specifications and standards.

Another common soft tissue injury involves damage to cartilage, which is a non-vascular, resilient, flexible connective tissue. Cartilage typically acts as a shock-absorber and/or sliding contact surface at articulating joints, but some types of cartilage provide support to tubular structures, such as for example, the larynx, air passages, and the ears. In general, cartilage tissue is comprised of cartilage cells, known as chondrocytes, located in an extracellular matrix composed of collagen, a structural scaffold, and aggrecan, a space-filling proteoglycan. Several types of cartilage can be found in the body, including hyaline cartilage, fibrocartilage and elastic cartilage. Hyaline cartilage is generally found in the body as articular cartilage, costal cartilage, and temporary cartilage (i.e., cartilage that is ultimately converted to bone through the process of ossification). Fibrocartilage is a transitional tissue that is typically located between tendon and bone, bone and bone, and hyaline cartilage and hyaline cartilage. Elastic cartilage, which contains elastic fibers distributed throughout the extracellular matrix, is typically found in the epiglottis, the ears and the nose.

One common example of hyaline cartilage injury is a traumatic focal articular cartilage defect to the knee. A strong impact to the joint can result in the complete or partial removal of a cartilage fragment of various size and shape. Damaged articular cartilage can severely restrict joint function, cause debilitating pain and may result in long term chronic diseases such as osteoarthritis, which gradually destroys the cartilage and underlying bone of the joint. Injuries to the articular cartilage tissue will typically not heal spontaneously and require surgical intervention if symptomatic. The current modality of treatment consists of lavage, removal of partially or completely unattached tissue fragments. In addition, the surgeon will often use a variety of methods such as abrasion, drilling or microfractures, to induce bleeding into the cartilage defect and formation of a clot. It is believed that the cells coming from the marrow will form a scar-like tissue called fibrocartilage that can provide temporary relief to some symptoms. Unfortunately, the fibrocartilage tissue does not have the same mechanical properties as hyaline cartilage and degrades faster over time as a consequence of wear. Patients typically have to undergo repeated surgical procedures which can lead to the complete deterioration of the cartilage surface. More recently, experimental approaches involving the implantation of autologous chondrocytes have been used with increasing frequency. The process involves the harvest of a small biopsy of articular cartilage in a first surgical procedure, which is then transported to a laboratory specialized in cell culture for amplification. The tissue biopsy is treated with enzymes that will release the chondrocyte cells from the matrix, and the isolated cells will be grown for a period of 3 to 4 weeks using standard tissue culture techniques. Once the cell population has reached a target number, the cells are sent back to the surgeon for implantation during a second surgical procedure. This manual labor-intense process is extremely costly and time consuming. Although, the clinical data suggest long term benefit for the patient, the prohibitive cost of the procedure combined with the traumatic impact of two surgical procedures to the knee, has hampered adoption of this technique.

Another example of cartilage injury is damage to the menisci of a knee joint. The meniscus is a C-shaped concave fibrocartilage tissue that is found between two bone ends of the leg, the femur and tibia. There are two menisci of the knee joint, a medial and a lateral meniscus. In addition to the menisci of the knee joint, fibrocartilage tissue can also be found in the acromioclavicular joint, i.e., the joint between the clavicle and the acromion of the scapula, in the sternoclavicular joint, i.e., the joint between the clavicle and the sternum, in the temporomandibular joint, i.e., the joint of the lower jaw, and in the intervertebral discs which lie between the vertebral bodies in the spine. The primary functions of meniscal cartilage are to bear loads, to absorb shock and to stabilize a joint. Meniscal tears of the knee often result from sudden traumatic injury, especially in association with ligament injuries, or due to the degeneration of the tissue. Meniscal tears often cause joint pain and catching or locking of the joint. If not treated properly, an injury to the meniscus, such as a "bucket-handle tear" in the knee joint, may lead to the development of osteoarthritis. Current conventional treatments for damaged meniscal cartilage include the removal and/or surgical repair of the damaged cartilage. Other less established or unproven techniques include allografts and collagen-based implants.

Synthetically based, non-absorbable materials have been developed as an alternative to biologically derived products. Although patches or implants made from such synthetically based non-absorbable materials are useful to repair some herniations, they are found to be inadequate in repairs made in regions such as the pelvic floor due to the fact that the patches or implants are made from non-bioabsorbable materials and may lead to undesirable tissue erosion and abrasion. Tissue erosion and abrasion may be counteracted by the use of patches, substrates, and implants manufactured from bioabsorbable materials.

There continues to be a need for bioabsorbable tissue repair implant devices having sufficient structural integrity and sufficiently long residence time to effectively withstand the stresses associated with implantation into an affected area. There is also a continuing need for bioabsorbable tissue repair implant devices that minimize or eliminate long-term erosion and abrasion (or other pathology) to the tissues in the surrounding area.

Bioabsorbable, porous foams may be used as implants to facilitate tissue growth. Bioabsorbable, foamed tissue engineered implant devices that have been reinforced to increase mechanical properties are disclosed in U.S. Pat. No. 6,599,323 entitled "Reinforced Tissue Implants and Methods of Manufacture and Use" issued Jul. 29, 2003, and also disclosed in U.S. patent application Ser. No. 09/747,488 entitled "Reinforced Foam Implants with Enhanced Integrity for Soft Tissue Repair and Regeneration" filed Dec. 21, 2000, the disclosures of both of which are incorporated by reference. Methods for manufacturing the foam component of the tissue implant include a variety of methods known and used in this art. For example, they include lyophilization, supercritical solvent foaming, extrusion or mold foaming (e.g. external gas injection or in situ gas generation), casting with an extractable material (e.g., salts, sugar or similar suitable materials) and the like.

Of particular utility is foam formation by freeze drying or lyophilization. The advantages of lyophilization include the avoidance of elevated temperatures, thus minimizing the potential for temperature-associated degradation and enabling the inclusion of temperature sensitive bioactive agents. Additional advantages include the ability to control the pore size and porosity of the foamed material. Non-aqueous lyophilization also eliminates the need for exposure of the processed material to water as is required in salt leaching processes, which may cause premature hydrolysis. Lyophilization is a cost effective, simple, one-step process that facilitates manufacturing, and is widely known and used in the food and pharmaceutical industries.

Lyophilization is a process for removing a (frozen or crystallized) solvent, frequently water, from various materials. Lyophilization of enzymes, antibodies, and sensitive biological materials is quite often the method of choice for extending the shelf life of these products and preserving their biological activity. As practiced as a means of foam formation, the lyophilization process usually requires that a polymeric material be rendered soluble in a crystallizable solvent capable of being sublimed, usually at reduced pressure. Although the solvent may be water, 1,4-dioxane is commonly used. This solvent has found great utility in foam formation because many medically important polymers are soluble in it. It is crystallizable (melting point approximately 12° C.), and it can generate a significant vapor pressure at temperatures in which it is still a solid, i.e. it can be sublimed at reduced pressure.

It will be generally recognized by one with ordinary skill, however, that lyophilization has certain limitations when applied to the manufacture of reinforced tissue engineered implant devices. For example, reinforcing elements must have limited solubility in the solvent employed. The integrity of reinforcing elements must withstand exposure to a solvent for the duration of the lyophilization process, otherwise the reinforcing elements (e.g., fibers, mesh, etc.) quickly lose their strength, and thus the advantages that the reinforcement is meant to provide. Selection of appropriate reinforcing materials may overcome at least one aspect of this problem. For example, absorbable polyglycolide (also known as polyglycolic acid) fibers, do not readily dissolve in many solvents and, in particular, do not dissolve in 1,4-dioxane. This property of polyglycolide fiber allows it to function as a suitable reinforcing element in many applications. Typically the fibers will be used in conjunction with a matrix polymer that is necessarily soluble in the same lyophilization solvent in which the fibers are not soluble. The matrix polymer, for example polylactide, is then capable of being foamed about these non-dissolving fibers during a lyophilization process.

However, bioabsorbable polyglycolide reinforcing elements are not acceptable for all surgical repairs. In some surgical applications, for example, they lose their mechanical strength too quickly after implantation. There is a need for bioabsorbable surgical devices in the form of a mechanically reinforced foam that retain their mechanical strength for extended periods of time after implantation to facilitate slow-to-heal tissue repairs. Surgical procedures requiring extended healing time include various soft tissue injury repairs, for example, damage to the pelvic floor, ligament or tendon tears, cartilage tears, and rotator cuff tears. Polylactide or certain lactide-rich lactide/glycolide copolymers such as 95/5 poly(lactide-co-glycolide), can be made into reinforcing elements that retain their strength for prolonged time periods. These polymers, however, readily dissolve in the commonly-used lyophilization solvent, 1,4-dioxane (also known as p-dioxane). Methods for making such reinforced foamed devices have not been discovered.

There continues to be a need in this art for bioabsorbable foam tissue repair implants having sufficient structural integrity that is sufficient to effectively withstand the stresses associated with implantation into an affected body area, and that can retain their mechanical strength for a sufficient time for use in slow-to-heal tissue repairs, and that can be made, at least in part, by lyophilization.

SUMMARY OF THE INVENTION

A bioabsorbable, reinforced tissue implant is disclosed. The tissue implant has a biocompatible polymeric foam and a biocompatible polymeric reinforcement member. The foam being soluble in a lyophilizing solvent and the reinforcement member being soluble in the lyophilizing solvent. Optionally, the fiber is coated with a biocompatible polymeric material having limited solubility in the lyophilizing solvent.

Yet another aspect of the present invention is a method for manufacturing a bioabsorbable, reinforced tissue implant. A solution of a foam-forming, biocompatible polymer in a lyophilizing solvent is provided. The solvent has a freezing point. A biocompatible polymeric reinforcement member is additionally provided. The reinforcement member and the foam are soluble in the lyophilizing solvent. The polymeric reinforcement member is placed in a cavity of a suitable mold. The solution is added to the cavity of the mold such that at least a part of the cavity is filled with the solution and at least part of the reinforcing member is in contact with the solution. The reinforcement member and solution are quenched to below the freezing point of the solvent, and then are lyophilized.

In yet another aspect of making a bioabsorbable, reinforced tissue implant, the polymeric reinforcement member is coated with a biocompatible polymeric material having limited solubility in the solvent used in the lyophilization process. The polymeric coating can be applied to the polymeric reinforcement member by coating methods including melt coating, spraying, solution methods, electrodeposition, vapor deposition, and/or powder coating. In the case of solution methods, the polymeric coating resin is generally required to be soluble in the solvent used in the coating process, while the polymeric reinforcement member usually has only limited solubility.

Yet another aspect of the present invention is a method for manufacturing a bioabsorbable, reinforced tissue implant. A solution of a foam-forming, biocompatible polymer in a lyophilizing solvent is provided. The solvent has a freezing point. A biocompatible polymeric reinforcement member is additionally provided. The reinforcement member and the foam are soluble in the lyophilizing solvent. The reinforcement member is coated with a biocompatible polymeric coating, wherein the coating has limited solubility in the lyophilizing solvent. The polymeric reinforcement member is placed in a cavity of a suitable mold. The solution is added to the cavity of the mold such that at least a part of the cavity is filled with the solution and at least part of the reinforcing member is in contact with the solution. The reinforcement member and solution are quenched to below the freezing point of the solvent, and then are lyophilized.

Still yet another aspect of the present invention is a method of repairing damaged tissue, particularly damaged soft tissue. A biocompatible tissue implant is provided. The implant has a biocompatible polymeric foam component and a biocompatible reinforcement member. The polymeric foam and the reinforcement member are soluble in the same lyophilizing solvent. The fiber is coated with a biocompatible polymeric material having limited solubility in the lyophilizing solvent. The implant is then placed in a desired position at a site relative to a tissue injury These and other aspects and advantages of the present invention will be more apparent by the following description and accompanying drawings.

BRIEF DESCRIPTION OF THE DRAWINGS

FIG. 10($b$) is a photographic depiction of poly(p-dioxanone) coated, 5 mil 95/5 poly(lactide-co-glycolide) fiber tied into a knot, the coating thickness is 1.75 mil.

FIG. 10($c$ is a photographic depiction of poly(p-dioxanone) coated, 5 mil 95/5 poly(lactide-co-glycolide) fiber tied into a knot, the coating thickness is 2.375 mil.

FIG. 10(d) is a photographic depiction of poly(p-dioxanone) coated, 5 mil 95/5 poly(lactide-co-glycolide) fiber tied into a knot, the coating thickness is 4.0 mil.

DETAILED DESCRIPTION OF THE INVENTION

The present invention relates to a biocompatible tissue implant or "scaffold" device which, preferably, is bioabsorbable, and to methods for making and using such a device. The implant includes one or more layers of a bioabsorbable polymeric foam having pores with an open or closed cell pore structure. A reinforcement component or components are also present within the implant to contribute enhanced mechanical and handling properties. The reinforcement component is preferably in the form of a mesh fabric that is biocompatible. The reinforcement component is preferably bioabsorbable as well.

In many surgical applications, for example such as for use as a reinforcement material for repair of the pelvic floor or rotator cuff, the tissue implants of the invention should have sufficient mechanical integrity to be effectively handled in the operating room, and they must be able to be sutured without tearing. Additionally, the implants should have sufficient burst strength to effectively reinforce the tissue, and the structure of the implant must be suitable to encourage tissue ingrowth. A preferred tissue ingrowth-promoting structure is one where the cells of the foam component are open and sufficiently sized to permit cell ingrowth. A suitable pore size is one that is sufficiently effective and in which the pores have an average diameter in the range of typically about 10 to 1000 microns and, more preferably, about 50 to 500 microns.

Figure 1:
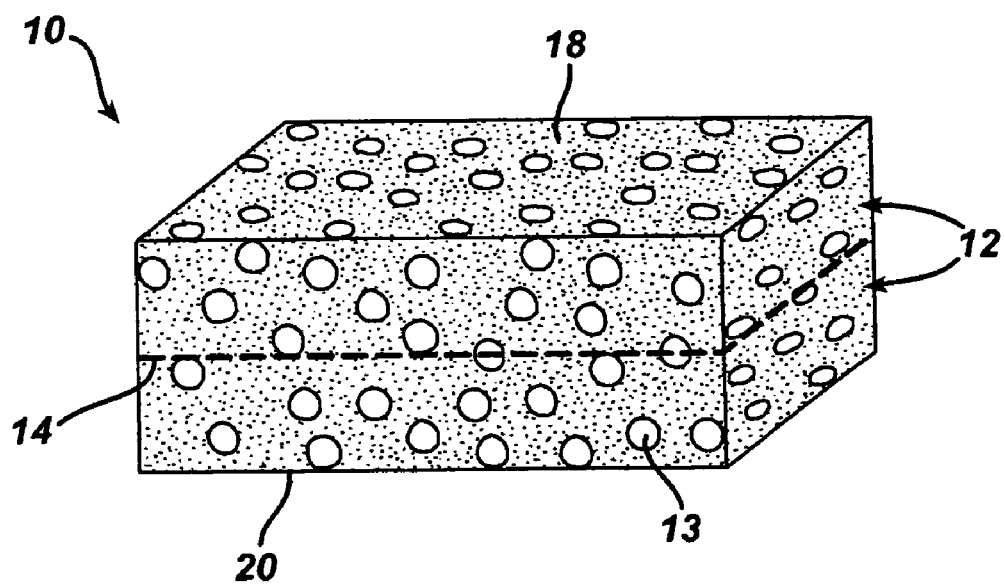
FIG. 1 is a perspective view of a reinforced tissue implant of the present invention.
Figure 2:
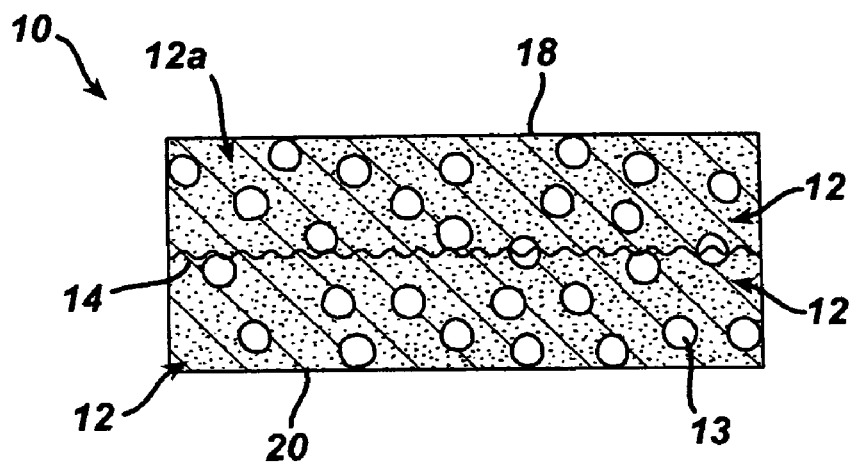
FIG. 2 is a cross-sectional view of the tissue implant device of FIG. 1.
Figure 3:
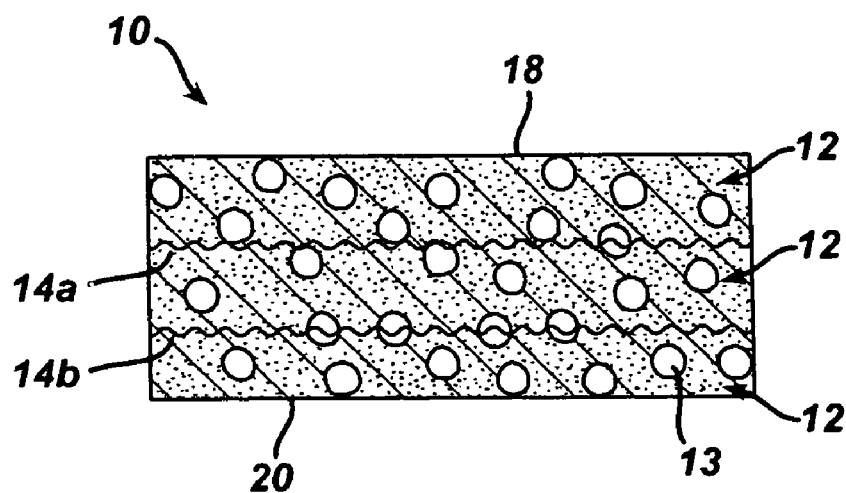
FIG. 3 is a cross-sectional view of an alternative embodiment of a tissue implant of the present invention.

In general, the shape and size of the scaffold will preferably closely mimic the size and shape of the defect it is trying to repair, although the shape and size may be substantially smaller or larger. For a rotator cuff repair, for example, it may be preferable to use a sheet configuration such as a rectangular patch, or a circular patch that can be further cut to size. Preferably, the strength of the reinforcement should be highest and stiffest in the direction parallel to the collagen fiber direction of the tendon. Referring to FIGS. 1 through 4, the implant 10 includes a polymeric foam component 12 and a reinforcement member 14. The foam component preferably has pores 13 with an open cell pore structure. Although illustrated as having the reinforcement component disposed substantially in the center of a cross section of the implant, it is understood that the reinforcement material can be disposed at any location within the implant. Further, as shown in FIG. 3, more than one layer of each of the foam component 12a, 12b and reinforcement component 14a, 14b may be present in the implant. It is understood that various layers of the foam component and/or the reinforcement material may be made from different materials.

Figure 4:
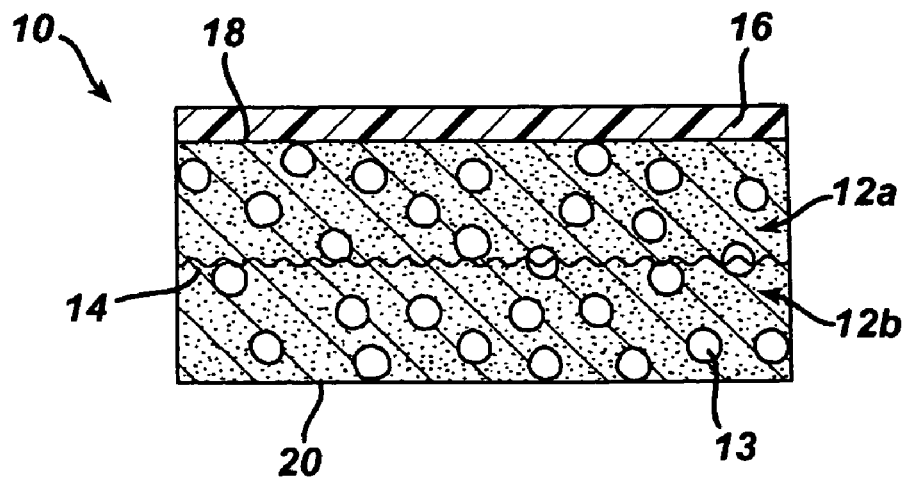
FIG. 4 is a cross-sectional view of yet another embodiment of a tissue implant of the present invention.

FIG. 4 illustrates an embodiment in which a barrier layer 16 is present in the implant. Although illustrated as being only on one surface of the implant 10, the barrier layer 16 may be present on either or both of the top and bottom surfaces 18, of the implant.

Figure 5:
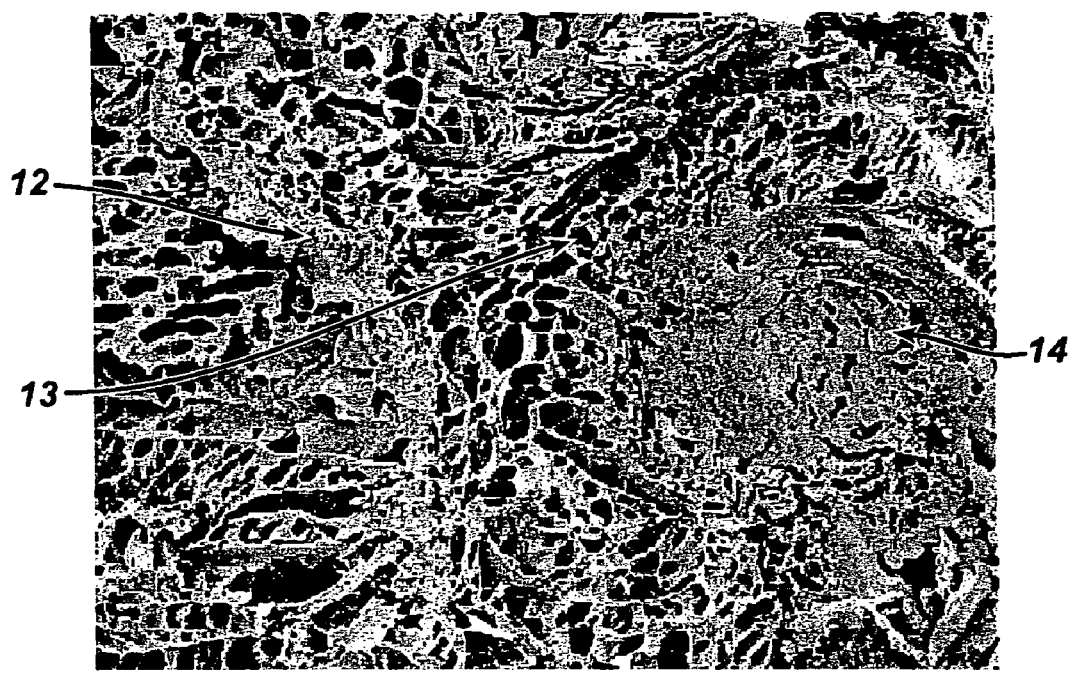
FIG. 5 is a scanning electron micrograph of a section of an implant according to the present invention.

The implant 10 must have sufficient structural integrity and physical properties to effectively facilitate ease of handling in an operating room environment, and to permit it to accept and retain sutures without tearing. Adequate strength and physical properties are developed in the implant through the selection of materials used to form the foam and reinforcement components, and the manufacturing process. As shown in FIG. 5, the foam component 12 is integrated with the reinforcement component 14 such that the pores 13 of the foam component penetrate the mesh of the reinforcement component 14 and interlock with the reinforcement component. The walls in adjacent layers of the foam component also interlock with one another, regardless of whether the foam layers are separated by a layer or reinforcement material or whether they are made from the same or different materials.

The bioabsorbable polymers that can be used to make porous, reinforced tissue engineered implant or scaffold devices according to the present invention include conventional biocompatible, bioabsorbable polymers including f aliphatic polyesters, poly(amino acids), copoly(ether-esters), polyalkylene oxalates, polyalkylene diglycolates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarates), absorbable poly(ester urethanes), biomolecules (i.e., biopolymers such as collagen, elastin, bioabsorbable starches, etc.) and blends thereof, copolymers thereof and the like.

As used herein, the term "polyglycolide" is understood to include polyglycolic acid. Further, the term "polylactide" is understood to include polymers of L-lactide, D-lactide, meso-lactide, blends thereof, and lactic acid polymers and copolymers in which other moieties are present in amounts less than 50 mole percent.

Currently, aliphatic polyesters are among the preferred absorbable polymers for use in making the foam portion of the foam implants according to the present invention. Aliphatic polyesters can be homopolymers, copolymers (random, block, segmented, tapered blocks, graft, triblock, etc.) having a linear, branched or star structure. Suitable monomers for making aliphatic homopolymers and copolymers include, but are not limited, to lactic acid (both L- and D-isomers), lactide (including L-, D-, and meso-lactide), glycolic acid, glycolide, ε-caprolactone, p-dioxanone (1,4-dioxan-2-one), trimethylene carbonate (1,3-dioxan-2-one), and combinations thereof and the like.

Elastomeric copolymers are also particularly useful in the present invention. Suitable elastomeric polymers include those with an inherent viscosity of 1.2 dL/g or greater, more preferably about 1.2 dL/g to 4 dL/g and most preferably about 1.4 dL/g to 2 dL/g, as determined at 25° C. in a 0.1 gram per deciliter (g/dL) solution of polymer in hexafluoroisopropanol (HFIP). Further, suitable elastomers exhibit a high percent elongation and a low modulus, while possessing good tensile strength and good recovery characteristics. In the preferred embodiments of this invention, the elastomer from which the foam component is formed exhibits a percent elongation (e.g., greater than about 200 percent and preferably greater than about 500 percent). In addition to these elongation and modulus properties, suitable elastomers preferably have a tensile strength greater than about 500 psi, preferably greater than about 1,000 psi, and a tear strength of greater than about 50 lbs/inch, preferably greater than about 80 lbs/inch.

Exemplary bioabsorbable, biocompatible elastomers include but are not limited to elastomeric copolymers of ε-caprolactone and glycolide (including polyglycolic acid) with a mole ratio of ε-caprolactone to glycolide of from about 35/65 to about 65/35, more preferably from 45/55 to 35/65; elastomeric copolymers of ε-caprolactone and lactide (including L-lactide, D-lactide, blends thereof, and lactic acid polymers and copolymers) where the mole ratio of ε-caprolactone to lactide is from about 30/70 to about 95/5 and more preferably from 30/70 to 45/55 or from about 85/15 to about 95/5; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40/60 to about 60/40; elastomeric copolymers of ε-caprolactone and p-dioxanone where the mole ratio of, ε-caprolactone to p-dioxanone is from about from 30/70 to about 70/30; elastomeric copolymers of p-dioxanone and trimethylene carbonate where the mole ratio of p-dioxanone to trimethylene carbonate is from about 30/70 to about 70/30; elastomeric copolymers of trimethylene carbonate and glycolide (including polyglycolic acid) where the mole ratio of trimethylene carbonate to glycolide is from about 30/70 to about 70/30; elastomeric copolymers of trimethylene carbonate and lactide (including L-lactide, D-lactide, blends thereof, and lactic acid polymers and copolymers) where the mole ratio of trimethylene carbonate to lactide is from about 30/70 to about 70/30; and blends thereof and the like.

It is to be understood that the exemplary bioabsorbable, biocompatible elastomers may be generally synthesized by a ring-opening polymerization of the corresponding lactone monomers or by polycondensation of the corresponding hydroxy-acids, or by combinations of these two polymerization methodologies.

One of ordinary skill in the art will appreciate that the selection of a suitable polymer or copolymer for forming the foam depends on several factors. The more relevant factors in the selection of the appropriate polymer(s) that is used to form the foam component include bioabsorption (or bio-degradation) kinetics; in-vivo mechanical performance; cell response to the material in terms of cell attachment, proliferation, migration and differentiation; and biocompatibility. Other relevant factors, which to some extent dictate the in-vitro and in-vivo behavior of the polymer, include the chemical composition, spatial distribution of the constituents, the molecular weight of the polymer, and the degree of crystallinity.

The ability of the material substrate to resorb in a timely fashion in the body environment is critical. But the differences in the absorption time under in-vivo conditions can also be the basis for combining two different copolymers. For example, a copolymer of 35/65 ε-caprolactone and glycolide (a relatively fast absorbing polymer) is blended with 40/60 ε-caprolactone and L-lactide copolymer (a relatively slow absorbing polymer) to form a foam component. Depending upon the processing technique used, the two constituents can be randomly inter-connected bicontinuous phases, or the constituents could have a gradient-like architecture in the form of a laminate type composite with a well-integrated interface between the two constituent layers. The microstructure of these foams can be optimized to regenerate or repair the desired anatomical features of the tissue that is being engineered.

In one embodiment it is desirable to use polymer blends to form structures which transition from one composition to another composition in a gradient-like architecture. Foams having this gradient-like architecture are particularly advantageous in tissue engineering applications to repair or regenerate the structure of naturally occurring tissue such as cartilage (articular, meniscal, septal, tracheal, etc.), esophagus, skin, bone, and vascular tissue. For example, by blending an elastomer of ε-caprolactone-co-glycolide with ε-caprolactone-co-lactide (e.g., with a mole ratio of about 5/95) a foam may be formed that transitions from a softer spongy material to a stiffer more rigid material in a manner similar to the transition from cartilage to bone. Clearly, one of ordinary skill in the art will appreciate that other polymer blends may be used for similar gradient effects, or to provide different gradients (e.g., different absorption profiles, stress response profiles, or different degrees of elasticity). Additionally, these foam constructs can be used for organ repair replacement or regeneration strategies that may benefit from these unique tissue implants. For example, these implants can be used for spinal disc, cranial tissue, dura, nerve tissue, liver, pancreas, kidney, bladder, spleen, cardiac muscle, skeletal muscle, tendons, ligaments and breast tissues.

The reinforcing component of the tissue implant of the present invention is comprised of any absorbable polymer that is normally soluble in the lyophilizing solvent. Of particular utility are the lactide-rich polymers and copolymers. This reinforcing component can be in any form including particles, fibers, sheets, nonwovens, and textiles with woven, knitted, warped knitted (i.e., lace-like), non-woven, and braided structures. In an exemplary embodiment of the reinforcing component has a mesh-like structure. In a preferred embodiment, the reinforcing component has the structure of a non-woven, where the fibers are generally interlocked by mechanical means, such as needle punching or crimping. Alternatively, the assembly of textile fibers may be held together by fusion. In any of the above structures, mechanical properties of the material can be altered by changing the density or texture of the material, or by embedding particles in the material. The fibers used to make the reinforcing component can be monofilaments, multifilaments, yarns, threads, pre-constructed architectures of fibers, such as braids, or bundles. These fibers can be made of any biocompatible materials such as polylactide, polylactic acid, polycaprolactone, copolymers or blends thereof. In one embodiment, the fibers are formed from a lactide/glycolide copolymer at a 95/5 mole ratio [95/5 poly(lactide-co-glycolide)]. In an additional embodiment, two or more different types of fiber are used as the reinforcing elements of the tissue implant.

The reinforcing material may also be formed from a thin, perforation-containing elastomeric sheet with perforations to allow tissue ingrowth. Such a sheet could be made of blends or copolymers of polylactic acid, and polycaprolactone.

In one embodiment, filaments that form the reinforcing material may be co-extruded to produce a filament with a sheath/core construction. Such filaments are comprised of a sheath of biodegradable polymer that surrounds one or more cores comprised of another biodegradable polymer. This may be desirable in instances where extended support is necessary for tissue ingrowth One of ordinary skill in the art will appreciate that one or more layers of the reinforcing material may be used to reinforce the tissue implant of the invention. In addition, biodegradable reinforcing layers (e.g., meshes or non-wovens) of the same structure and chemistry or different structures and chemistries can be overlaid on top of one another to fabricate reinforced tissue implants with superior mechanical strength or provide directional properties.

The steps involved in the preparation of these foams include choosing the appropriate solvents for the polymers to be lyophilized and preparing a homogeneous solution. Next, the polymer solution is subjected to a freezing and vacuum drying cycle. The freezing step phase separates the polymer solution and vacuum drying step removes the solvent by sublimation and/or drying, leaving a porous polymer structure or an interconnected open cell porous foam.

Suitable solvents that may be used ideally will have high vapor pressure at temperatures below the freezing point of the solvent and a freezing point reasonably obtainable by commercially available equipment. In the practice of the present invention such solvents may include p(dioxane) and trioxane.

The applicable polymer concentration or amount of solvent that may be utilized will vary with each system. Generally, the amount of polymer in the solution can vary from about 0.5% to about 90% and, preferably, will vary from about 0.5% to about 30% by weight, depending on factors such as the solubility of the polymer in a given solvent and the final properties desired in the foam.

In one embodiment, solids may be added to the polymer-solvent system to modify the composition of the resulting foam surfaces. As the added particles settle out of solution to the bottom surface, regions will be created that will have the composition of the added solids, not the foamed polymeric material. Alternatively, the added solids may be more concentrated in desired regions (i.e., near the top, sides, or bottom) of the resulting tissue implant, thus causing compositional changes in all such regions. For example, concentration of solids in selected locations can be accomplished by adding metallic solids to a solution placed in a mold made of a magnetic material (or vice versa). Settling out can be controlled in a number of ways including agitaton and other methods well known to those skilled in the art.

A variety of types of solids can be added to the polymer-solvent system. Preferably, the solids are of a type that will not react with the polymer or the solvent. Generally, the added solids have an average diameter of less than about 1.0 mm and preferably will have an average diameter of about 50 to about 500 microns. Preferably the solids are present in an amount such that they will constitute from about 1 to about 50 volume percent of the total volume of the particle and polymer-solvent mixture (wherein the total volume percent equals 100 volume percent).

Exemplary solids include, but are not limited to, particles of demineralized bone, calcium phosphate particles, calcium sulfate particles, Bioglass™ particles or calcium carbonate particles for bone repair, leachable solids for additional pore creation and particles of bioabsorbable polymers not soluble in the solvent system that are effective as reinforcing materials or to create pores as they are absorbed and non-bioabsorbable materials.

Suitable leachable solids include nontoxic leachable materials such as salts (e.g., sodium chloride, potassium chloride, calcium chloride, sodium tartrate, sodium citrate, and the like), biocompatible mono and disaccharides (e.g., glucose, fructose, dextrose, maltose, lactose and sucrose), polysaccharides (e.g., starch, alginate, chitosan), water-soluble proteins (e.g., gelatin and agarose), and acid soluble proteins (e.g. collagen). The leachable materials can be removed by immersing the foam with the leachable material in a solvent in which the particle is soluble for a sufficient amount of time to allow leaching of substantially all of the particles, but which does not dissolve or detrimentally alter the foam. The preferred extraction solvent is water, most preferably distilled-deionized water. Preferably the foam will be dried after the leaching process is complete at low temperature and/or vacuum to minimize hydrolysis of the foam unless accelerated absorption of the foam is desired. Optionally, it may be desirable to not fully leach all the solid from the scaffold before implantation, for example if after implantation of the scaffold, the remainder of leachable solids can and provide a therapeutic effect at the implantation site. For example, calcium chloride is a well-known factor to active platelets. A scaffold containing calcium chloride may be able to cause platelet aggregation, which will cause release of growth factors, without the addition of thrombin.

Suitable non-bioabsorbable materials include biocompatible metals such as stainless steel, cobalt chrome, titanium and titanium alloys, and bio-inert ceramic particles (e.g., alumina, zirconia, and calcium sulfate particles). Further, the non-bioabsorbable materials may include particles made from polymers such as polyethylene, polyvinylacetate, polyethylene oxide, polymethylmethacrylate, silicone, polyethylene glycol, polyurethanes, polypropylene, and natural biopolymers (e.g., cellulose particles, chitin, and keratin), and fluorinated polymers and copolymers (e.g., polyvinylidene fluoride).

It is also possible to add solids (e.g., barium sulfate) that will render the tissue implants radio-opaque. The solids that may be added also include those that will promote tissue regeneration or regrowth, as well as those that act as buffers, reinforcing materials or porosity modifiers.

As noted above, porous, reinforced tissue implant devices of the present invention are made by injecting, pouring, or otherwise placing, the appropriate polymer solution into a mold set-up comprised of a mold and the reinforcing elements of the present invention. The mold set-up is cooled in an appropriate bath or on a refrigerated shelf and then lyophilized, thereby providing a reinforced tissue engineered scaffold. In the course of forming the foam component, it is believed to be important to control the rate of freezing of the polymer-solvent system. The type of pore morphology that is developed during the freezing step is a function of factors such as the solution thermodynamics, freezing rate, temperature to which it is cooled, concentration of the solution, and whether homogeneous or heterogenous nucleation occurs. One of ordinary skill in the art can readily optimize the parameters without undue experimentation.

The required general processing steps include the selection of the appropriate materials from which the polymeric foam and the reinforcing components are made. If a mesh reinforcing material is used, the proper mesh density must be selected. Further, the reinforcing material must be properly aligned in the mold, the polymer solution must be added at an appropriate rate and, preferably, into a mold that is tilted at an appropriate angle to minimize the formation of air bubbles, and the polymer solution must be lyophilized.

In embodiments that utilize a mesh reinforcing material, the reinforcing mesh advantageously has a certain density range. That is, the openings in the mesh material must be sufficiently dense to render the construct suturable, but not so dense as to impede proper penetration of the foam material and cells through the reinforcing mesh openings. Without proper bonding across the reinforcing element, the integrity of the layered structure is compromised leaving the construct fragile and difficult to handle.

Details of the processing steps currently used to make absorbable mesh reinforced foam scaffolds with non-soluble reinforcing elements are discussed in previously mentioned U.S. patent application Ser. No. 09/747,488 and U.S. Pat. No. 6,599,323.

This disclosure specifically relates to a method of preparing such biocompatible, bioabsorbable tissue implants using reinforcing elements that are soluble in the lyophilizing solvent.

This novel process can be broken down into several main components including: selection of reinforcing elements based on diameter; annealing of reinforcing elements; tensioning the reinforcing elements; constraining the elements during processing; and finally pre-cooling and quenching the reinforcing element/solution system to limit the exposure of the reinforcing element to liquid solvent prior to lyophilization.

In yet another aspect of making a bioabsorbable, reinforced tissue implant, the polymeric reinforcement member is coated with a biocompatible polymeric materials having limited solubility in the lyophilization solvent. The coating can be applied using a variety of techniques known to those skilled in the art including melt coating, spraying, solution techniques, electrodeposition, vapor deposition, and/or powder coating.

Briefly, the implants are made by placing a reinforcement material within a stretcher and clamp apparatus in a desired position and orientation and if need be, under tension during processing. The stretcher and clamp apparatus is then placed in a mold to create a mold assembly. A solution of a desired polymeric material in a suitable solvent is prechilled prior to its addition to the mold assembly, which may also be prechilled, and the mold assembly is immediately quenched below the melting point of the solvent. Finally, the solution in the mold assembly is lyophilized to obtain the implant in which a reinforcement material is embedded in a polymeric foam. Each of the steps in this process will be covered in more detail in the following section.

The diameter of the reinforcing element will have a large impact on the to amount of surface area of reinforcing material that is directly exposed to the solvent. A larger diameter reduces the surface area that will be exposed to the solvent. For this reason, monofilament reinforcing elements may be preferred over yarns. In preferred embodiments the fiber will have a diameter in the range of 50 microns to 2 mm.

Annealing the reinforcing elements prior to lyophilization will further increase the resistance of the reinforcing material to dissolution. Annealing schemes that enhance the crystallinity level of the reinforcing fibers are of particular utility. For 95/5 poly(lactide-co-glycolide) reinforcing elements, an annealing cycle containing a step that holds the reinforcing materials at 120° C. under a nitrogen atmosphere for 3 hours is a preferred way to process these constructs.

Figure 6:
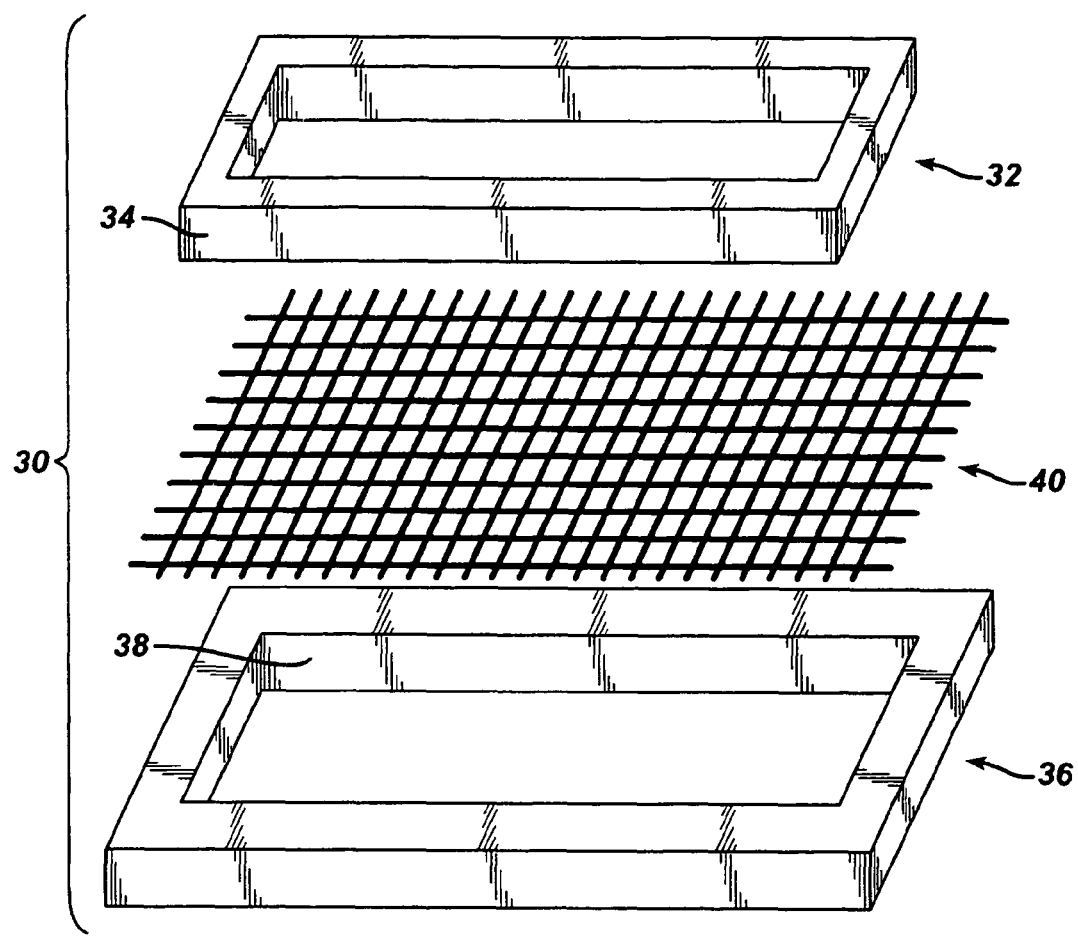
FIG. 6 is an exploded perspective view of a stretcher and clamp apparatus used to keep the reinforcing mesh flat, level, and under tension during manufacturing of a tissue implant of the present invention.

Constraining the soluble reinforcing elements during the lyophilization of the reinforced foam is another way to produce implants with the desired integrity and mechanical properties. Preferably, the reinforcement material is substantially flat when placed in the mold. One method, known in the art, to ensure the proper degree of flatness involves pressing flat the reinforcement material (e.g., mesh) using a heated press prior to its placement within the mold. This inventive method involves the use of a stretcher and clamp apparatus that constrains the reinforcement element flat. Such a stretcher and clamp apparatus 30 is depicted in FIG. 6.

Figure 7:
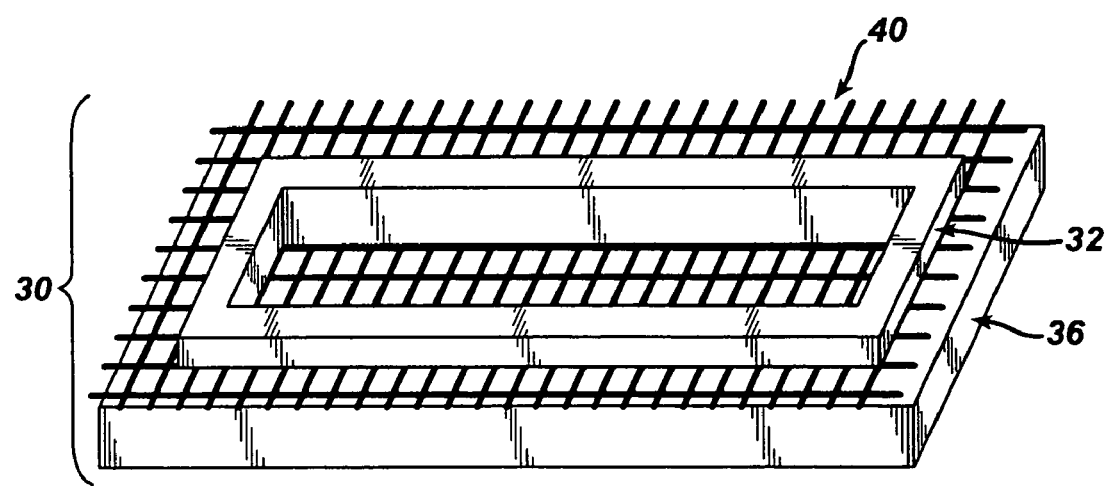
FIG. 7 is a view of the stretcher and clamp of FIG. 6 holding a mesh reinforcement.

Stretcher and clamp apparatus 30 is comprised of inner and outer frames 32,36. Inner frame 32 has outside surface 34, while outer frame 34 has inner surface 38. Mesh 40 is placed between frames 32,36 such that, as shown in FIG. 7, mesh 40 is engaged between inner surface 38 of outer frame 34 and outside surface 34 of inner frame 32.

Stretcher and clamp apparatus 30 keeps the reinforcement material flat, level, and constrained, with the ability to add tension, during processing. In addition, stretcher and clamp apparatus 30 make it possible to use a wider range of reinforcing materials, including those that have curled edges due to residual stresses in their structure. Another advantage that apparatus 30 provides is that mesh 40 placement within the foam can be precisely controlled, and easily changed, by using stretchers of different heights or by using a shim system.

As briefly aforementioned, it is not unexpected that a certain level of tension imparted on the mesh may play a role in strength retention of the reinforcement. This strength retention arises from the residual stresses imparted to the mesh during loading. In order to retain such tension after removal from the stretcher and clamp device, it is preferred to anneal the mesh while under tension. This can be achieved by suspending the mesh in an annealing oven and loading the mesh during annealing. After annealing but before removal of the suspended and loaded mesh, the stretcher and clamp apparatus can be affixed after which the assembly is subsequently removed from the oven. The optimum level of loading can be determined by experimentation.

Quenching the reinforcing element/solution system is a critical step to control the kinetics of the reinforcing element dissolution. This dissolution is dependent upon both exposure time and exposure temperature. To minimize these factors, the stretcher and clamp apparatus, containing the optimized reinforcing element, is quenched immediately after being placed in the pre-chilled solvent in the pre-chilled mold. By adding the quenching step, the initial exposure of the reinforcing fibers to the lyophilizing solvent can be limited.

The manner in which the polymer solution is added to the mold prior to lyophilization also contributes to the creation of a tissue implant with adequate mechanical integrity. Assuming that a mesh reinforcing material will be used, and that it will be oriented and positioned at a desired depth in the mold, the polymer solution is then poured in a way that allows air bubbles to escape from between the layers of the foam component. Preferably, the mold is tilted at a desired angle and pouring is affected at a controlled rate to best prevent bubble formation. One of ordinary skill in the art will appreciate that a number of variables will control the tilt angle and pour rate. Generally, the mold should be tilted at an angle of greater than about 1 degree to avoid bubble formation. In addition, the rate of pouring should be slow enough to enable any air bubbles to escape from the mold, rather than to be trapped in the mold.

A preferred composition for the reinforcing element is 95/5 poly(lactide-co-glycolide). Two fiber forms of this co-polymer were used in the examples below: a yarn with filaments with diameters on the order of 10 to 15 microns, and a monofilament with a diameter of 125 um.

When a mesh material is used as the reinforcing component, the density of the mesh openings is an important factor in the formation of a resulting tissue implant with the desired mechanical properties. A low density, or open knitted mesh material, is preferred. The density or "openness" of a mesh material can be evaluated using a digital photocamera interfaced with a computer. In one evaluation, the density of the mesh was determined using a Nikon SMZ-U Zoom with a Sony digital photocamera DKC-5000 interfaced with an IBM 300PL computer. Digital images of sections of each mesh magnified to 20× were manipulated using Image-Pro Plus 4.0 software in order to determine the mesh density. Once a digital image was captured by the software, the image was thresholded such that the area accounting for the empty spaces in the mesh could be subtracted from the total area of the image. The mesh density was taken to be the percentage of the remaining digital image. Implants with the most desirable mechanical properties were found to be those with a mesh density in the range of about 20% to 88% and more preferably about 20% to 55%. In this work, meshes were knitted from these fibers with a density of 45%.

Another aspect of the present invention is providing a biocompatible tissue implant in a method of repairing damaged tissue, particularly damaged soft tissue. The implant has a biocompatible polymeric foam component and a biocompatible reinforcement member. The polymeric foam and the reinforcement member are soluble in the same solvent. The implant is then placed in a desired position at a site relative to a tissue injury. The implant may be placed within a lesion that constitutes the tissue injury, or over the lesion, and may be of a size and shape such that it matches a geometry and dimension of the lesion.

Figure 8:
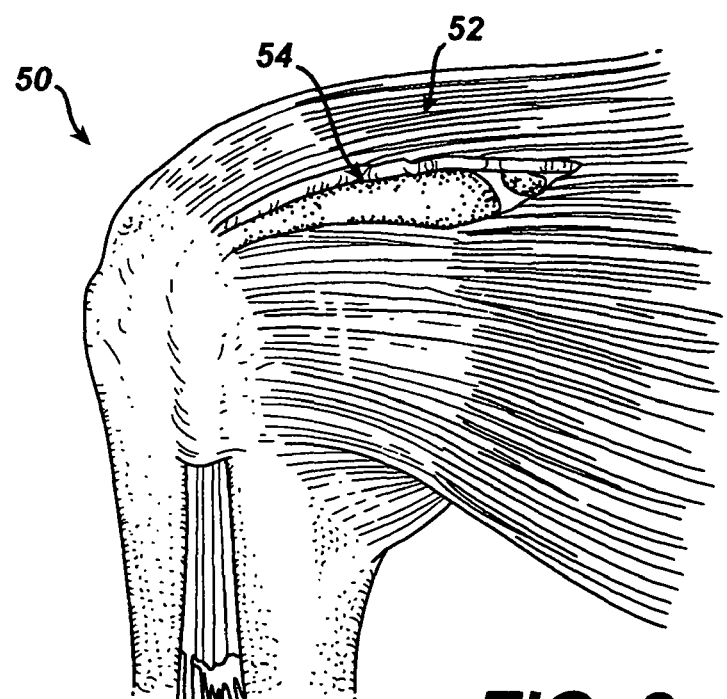
FIG. 8 is an illustration of a patient's shoulder with a tear in the rotator cuff tendon.
Figure 9:
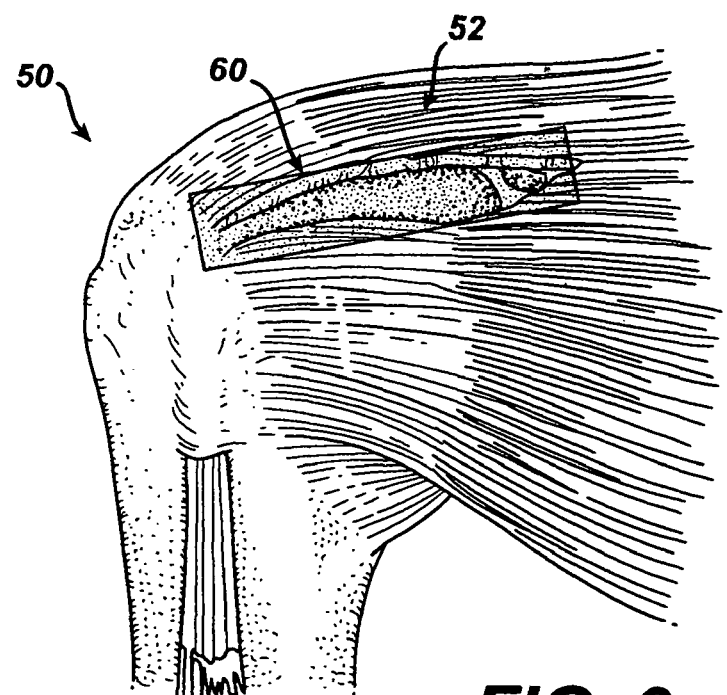
FIG. 9 is an illustration of an implant device of the present invention implanted in a patient's shoulder for repairing a tear in the rotator cuff tendon.

FIG. 8 shows a patient's shoulder 50, with lesion 54 in rotator cuff tendon 52. A method of repairing lesion 54, according to the present invention, is illustrated on FIG. 9. Here, implant 60 is placed over lesion 54, and affixed in place. The implant may also be placed within lesion 54 in an interference fit, or adjacent to lesion 54 that constitutes a tear such that the implant reinforces the tissue. Also, implant 60 may be wrapped around the tissue having lesion 54.

Affixing the implant to the damaged site may be accomplished by a number of methods including, but not limited to, suturing, stapling, or using a glue or a device selected from the group consisting of suture anchors, tissue tacks, darts, screws, arrows, and combinations thereof. The glue may be selected from fibrin glues, fibrin clots, platelet rich plasma, platelet poor plasma, blood clots, biologically compatible adhesives, and combinations thereof.

There are a number of embodiments of the present invention. Melt coating of a sheath resin onto a pre-existing fiber is a preferred method. It is advantageous to anneal the substrate fiber prior to melt coating. To avoid undo distortion of the fiber and too great a loss of molecular orientation, resulting in loss of mechanical strength. Another advantageous method is to solution coat of sheath resin onto pre-existing fiber. The solvent employed should be a solvent of the sheath resin but have limited affect on the substrate resin.

Another method is by co-extrusion, the simultaneous melt extrusion of at least two resins; that is, the simultaneous extrusion of a polymeric sheath layer and a polymeric core layer. In this case the fiber is not pre-existing at the time of coating application. The resulting extrudate generally requires drawing to increase molecular orientation to increase fiber strength.

Resin characteristics that are advantageous for the practice of the present invention include the following: low melting point, adhesion to substrate, rapid attainment of dimensional stability, appropriate glass transition temperature, appropriate solubility, and appropriate absorbability.

A low melting point is advantageous in that it is generally a prerequisite to a low melt extrusion temperature; a low melt extrusion temperature in turn helps to insure that the mechanical properties of the substrate fiber are not significantly diminished or lost. This latter effect is due to the loss of molecular orientation of the polymer chains of the substrate fiber at high coating temperatures. We have found that the polymer poly(p-dioxanone) possesses a low enough melting point to allow a low melt extrusion temperature, supporting a coating process that does not significantly decrease the tensile strength of 95/5 poly(lactide-co-glycolide) fibers. Note that it may be advantageous to adjust the line tension of the substrate fiber during the coating process.

It may be advantageous to have sufficient adhesion of the coating to the substrate to effectively prevent premature stripping of the coating or flaking. For example, a polyester coating of poly(p-dioxanone) adheres adequately to the polyester fiber of 95/5 poly(lactide-co-glycolide).

It may be advantageous to have rapid attainment of dimensional stability. In some cases this may be the rapid crystallization of a crystallizable coating resin. A polyester coating of poly(p-dioxanone) crystallizes sufficiently fast to allow the coated fiber to be effectively "taken-up" by conventional means without producing fiber that is tacky and self adhering.

It may be advantageous for the coating resin to have an appropriately low glass transition temperature. Coatings of high glass transition temperature polymers must be sufficiently thin to prevent the coating fiber from being too stiff. Materials having low glass transition temperature generally possess low Young's moduli allowing the coated fiber to be supple even when the thickness of the coating is substantial, an advantage in a number of surgical applications.

It may be advantageous to have appropriate solubility. In certain embodiments of the present invention, it is desirable to have the coating resin relatively insoluble in the solvent used in the foam formation process. As already pointed out, p-dioxane is a desirable solvent for the foam formation process of lyophilization. For example, a polyester coating of poly(p-dioxanone) has limited solubility in p-dioxane. In another embodiment, the coating is not applied by melt coating by can be applied by solvent coating. In this case, the resin must be soluble in a "coating solvent", but relatively insoluble in the "foam formation solvent", e.g., p-dioxane. Although polydioxanone, also known as poly(p-dioxanone), or poly(1,4-dioxanone), is a preferred coating copolymer, it should be evident to one possessing ordinary skill that other absorbable polymers may function as well. For instance, copolymers rich in polymerized p-dioxanone, might be used. These include, for instance, 95/5 poly(p-dioxanone-co-glycolide).

It may be advantageous to have appropriate absorbability. In the case of a substrate fiber that is absorbable, having a coating which is also absorbable may be advantageous. For example, the polyester poly(p-dioxanone) is absorbable making it particularly advantageous as a coating related to the present invention.

Although biologically active agents (e.g. drugs, pharmaceutical, antimicrobial agents) can be added to the foam components or to the reinforcing components, separately or in combination, it is particularly useful to add said agents to the polymeric coating of the reinforcing components, for those medical devices that employ polymeric coated reinforcing components. In the case of a melt applied polymeric coating, it is of further advantage that the polymeric coating be made of a resin exhibiting a relatively low melt viscosity at a relatively low processing temperature. Poly(p-dioxanone) is a relatively low melting synthetic absorbable polyester typically prepared by ring opening polymerization of the lactone, p-dioxanone. Copolymerization of this lactone with small amounts of another lactone such as lactide, trimethylene carbonate, or $\Sigma$-caprolactone, can result in a material of even lower melting. To ensure that the polymer melt exhibits a low melt viscosity, the molecular weight of the coating resin might be limited. Thus a random copolymer of 95/5 poly(p-dioxanone-co-lactide) with an inherent viscosity of about 1 dL/g, as measured in HFIP at 25° C. at a concentration of 0.1 g/dL might provide a particularly suitable coating resin for the present invention because of several desirable attributes including limited solubility in 1,4-dioxane, low melting temperature, low melt viscosity at a low melt coating process temperature.

The following examples are illustrative of the principles and practice of this invention although not limited thereto. Numerous additional embodiments within the scope and spirit of the invention will become apparent to those skilled in the art. The constructs made in each of the following examples are designated with a construct identification code according to Table 1.

TABLE 1

Construct Identification Codes

| | |
|---|---|
| 95/5 poly(lactide-co-glycolide) yarn mesh - unannealed, unquenched | YUU |
| 95/5 poly(lactide-co-glycolide) yarn mesh - unannealed, quenched | YUQ |
| 95/5 poly(lactide-co-glycolide) yarn mesh - annealed, unquenched | YAU |
| 95/5 poly(lactide-co-glycolide) yarn mesh - annealed, quenched | YAQ |
| 95/5 poly(lactide-co-glycolide) monofilament mesh - unannealed, unquenched | MUU |
| 95/5 poly(lactide-co-glycolide) monofilament mesh - unannealed, quenched | MUQ |
| 95/5 poly(lactide-co-glycolide) monofilament mesh - annealed, unquenched | MAU |
| 95/5 poly(lactide-co-glycolide) monofilament mesh - annealed, quenched | MAQ |

Example 1

Unannealed 95/5 Poly(Lactide-co-Glycolide) Yarn Mesh Unquenched and Quenched (Constructs YUU And YUQ)

This example describes the preparation of a three-dimensional elastomeric tissue implant with a 95/5 poly(lactide-co-glycolide) mesh reinforcement produced according to the methods described in the existing art and in the manner as described in this work, namely quenching the mold assembly after adding the polymer solution.

A solution of the polymer to be lyophilized to form the foam component of both constructs was prepared. A 5% solution (by weight) of 60/40 poly(lactide-co-caprolactone) in 1,4-dioxane was made in a flask placed in a water bath stirring at 60° C. for 5 hours. The solution was filtered using an extraction thimble and stored in a flask.

The mesh used as the reinforcement in the constructs of this example was made from 95/5 poly (lactide-co-glycolide) yarn. Pieces of the mesh, cut to dimensions slightly larger than the stretcher and clamp apparatus (5 cm by 14 cm), were solvent-scoured to remove lubricant finishes and foreign materials that accumulated during manufacturing using an agitated batch washing process in a Bransonic Ultrasonic Cleaner (Branson Ultrasonics Corp., Danbury, Conn.). For scouring, the mesh was placed in a plastic tray filled with isopropyl alcohol which was put into the ultrasonic cleaner. The temperature of the cleaner was held at 30° C. The mesh was then agitated in the ultrasonic cleaner for 30 minutes, rinsed with de-ionized water 3 times, and then re-agitated in a plastic tray filled with de-ionized water for 30 minutes. The mesh was then removed from the plastic tray and placed under vacuum overnight. Mesh was then placed in a stretcher and clamp apparatus used to keep the mesh taut and flat. The mesh in the stretcher and clamp apparatus were then set aside in a cool, dry environment.

Room temperature polymer solution was then added to aluminum molds (15.3 cm×15.3 cm). Into each mold, 10 g of the polymer solution was poured, ensuring that the solution completely covered the bottom of the mold. To prepare unquenched specimens (Code YUU), the mesh piece in its stretcher and clamp apparatus was then placed in a mold to form a mold assembly. The mold assembly was then transferred to a Virtis, Freeze Mobile G freezedryer (Virtis Inc., Gardiner, N.Y.) and the assembly was lyophilized according to the following cycle: 1) −17° C. for 15 minutes; 2) −15° C. for 60 minutes; 3) −5° C. for 60 minutes under vacuum 150 milliTorr; 4) 5° C. for 60 minutes under vacuum 150 milliTorr; 5) 20° C. for 60 minutes under vacuum 150 milliTorr.

To prepare quenched specimens (Code YUQ), several modifications to the above procedure were made. First, the mold was pre-chilled to −17° C. in the lyophilizer. Immediately prior to submersion in liquid nitrogen, the mold was taken out of the freezer, the mesh secured in the stretcher and clamp device was placed immediately in the pre-chilled mold and as concurrently as possible, the polymer solution was poured into the mold. The assembly was then immediately quenched in liquid nitrogen. The time between removing the pre-chilled mold from the lyophilizer and the time of quench was minimized. The mold containing the frozen polymer solution surrounding the mesh was transferred to the aforementioned lyophilizer and lyophilized according to the aforementioned cycle.

The mold assemblies were then removed from the freezer and placed in a nitrogen box overnight. Following the completion of this process the resulting constructs were carefully peeled out of the mold in the form of a foam/mesh sheet.

In this example, it was found that in the absence of the quenching step, a significant quantity of the yarn dissolved in the polymer solution in the time that it took for the lyophilizer to ramp down below the freezing point of the solvent. With the addition of the quenching step, the mesh survived exposure to the solvent and was present as a reinforcing element in the final construct. The minimization or substantial elimination of dissolution of the yarn results in substantial retention of the mechanical strength of the reinforcing mesh, thereby providing for sufficient mechanical characteristics when used as a reinforcing implant. The mechanical testing results are contained in Example 5 below.

Example 2

Annealed 95/5 Poly(Lactide-co-Glycolide) Yarn Mesh Unquenched and Quenched (Constructs YAU and YAQ)

This example is identical to Example 1 with the exception that in this example, the 95/5 poly(lactide-co-glycolide) yarn mesh was annealed prior to processing.

The meshes were scoured according to the procedure delineated in Example 1. The scoured meshes were placed in stretcher and clamp devices used to hold the meshes flat and taut. The mesh/device assemblies were then placed in an inert gas annealing oven and annealed at 120° C. for 3 hours. The remainder of the experiment was conducted in the same manner as Example 1 with one annealed mesh being left unquenched and the other mesh being quenched. The lyophilization cycle was also the same.

It was found that the addition of the quenching step resulted in reinforced constructs in which less dissolution of the reinforcing fibers took place. Without quenching, regions of the mesh were observed to begin to dissolve in the solvent.

The annealing step produced constructs with improved mechanical characteristics versus constructs without the annealing step. The testing of the mechanical properties is contained in Example 5 below.

Example 3

Unannealed 95/5 Poly(Lactide-co-Glycolide) Monofilament Mesh Unquenched and Quenched (Constructs MUU and MUQ)

The same procedure as described in Example 1 was used in this example with the exception that 95/5 poly(lactide-co-glycolide) monofilament was used to make the mesh instead of multifilament yarn. The only other difference was the size of the mold used. In this example, the same 5% (by weight) 60/40 poly(lactide-co-caprolactone) solution in 1,4-dioxane was poured into smaller aluminum molds (15.3 cm×7 cm). Therefore, 40 g of polymer solution was sufficient to fully cover the bottom of the mold. Again, the meshes were scoured according to the procedure delineated in Example 1, and the scoured monofilament meshes constrained by the stretcher and clamp device were placed into the polymer-containing molds. One mold was placed directly on the shelf of the lyophilizer after placement of the mesh and lyophilized according to the cycle delineated in Example 1. The other mesh was first quenched by placing the mold in a stainless steel tray of liquid nitrogen before the mold was put on the shelf of the lyophilizer. The frozen assembly was then lyophilized according to the same cycle as described in Example 1.

It was found that the addition of the quenching step resulted in reinforced constructs in which less dissolution of the reinforcing monofilaments took place. Without quenching, regions of the mesh were observed to begin to dissolve in the solvent, though the dissolution rate was much slower than that observed with the Example 1 yarn reinforced constructs processed without quenching.

Example 4

Annealed 95/5 Poly(Lactide-co-Glycolide) Monofilament Mesh Unquenched and Quenched (Constructs MAU and MAQ)

This example was almost identical to Example 3 with the exception that in this example, the 95/5 poly(lactide-co-glycolide) monofilament mesh was annealed prior to processing. The meshes were scoured according to the procedure delineated in Example 1. The scoured meshes were placed in stretcher and clamp devices used to hold the meshes flat and taut. The mesh/device assemblies were then placed in an inert gas annealing oven and annealed at 120° C. for 3 hours. One annealed monofilament mesh was placed in a large aluminum mold containing 100 g of the 5% (by weight) 60/40 poly (lactide-co-caprolactone) solution in 1,4-dioxane used in all of the examples, and this mold was placed on the shelf of the lyophilizer and lyophilized according to the cycle delineated in Example 1. The other monofilament mesh was placed in a small aluminum mold containing 40 g of the 5% (by weight) 60/40 poly(lactide-co-caprolactone) solution in 1,4-dioxane and was immediately quenched after submersion in the polymer solution. This frozen mold was then placed on the shelf of the lyophilizer and lyophilized according to the cycle delineated in Example 1.

It was found that the addition of the quenching step resulted in reinforced constructs in which less dissolution of the reinforcing elements took place. Without quenching, regions of the mesh were observed to begin to dissolve in the solvent, reducing the ability to act as a reinforcing element.

Example 5

Mechanical Properties of Yarn Mesh Constructs

This example describes the testing of mechanical properties of the reinforced meshes made in Examples 1 and 2. The components of the constructs were tested as controls. It is noted that the mesh controls were scoured according to the procedure outlined in Example 1.

Peak loads of constructs described in Examples 1 and 2 were measured using an Instron machine (Model 4501, Instron, Inc., Canton, Mass.), outfitted with a 20 lb. load cell. The specimens were cut (40 mm×9.9 mm) using a die cutter (with the exception of the mesh controls that were cut with scissors), the thickness of each specimen was measured prior to testing. Seven specimens of each control and construct type were measured. Pneumatic grips with rubber coated faces were used grip the samples such that a 20 mm gauge length, the length of the construct between the grips, was present at the start of the experiment. The grip pressure was set at 50 psi. The cross-head speed was one inch per minute.

Table 2 shows the peak loads for the controls and constructs formed with yarn meshes. The table shows that a construct could not be formed without annealing and quenching steps. When a quenching step is added, the peak load of a yarn-reinforced construct is measured to be 1.3 lb. The peak load is increased when the reinforcing yarn mesh is pre-annealed (7.0 lb). The addition of the annealing step without the quenching step also results in increased peak load (2.8 lb), although the improvement is greater with quenching.

TABLE 2

Mechanical Property Data

|  | Test Method | Peak load (lb) | STD (lb) | N |
|---|---|---|---|---|
| CONTROL |  |  |  |  |
| Foam | Tensile | 0.92 | 0.26 | 7 |
| Yarn Mesh, Scoured | Tensile | 12.58 | 2.13 | 7 |
| Yarn Mesh | Tensile | 16.98 | 2.42 | 4 |
| Annealed Yarn Mesh | Suture Pull Out, 90 Degree Testing Direction | 10.51 | 0.53 | 3 |
| Annealed Yarn Mesh | Suture Pull Out, 0 Degree Testing Direction | 7.92 | 1.65 | 4 |
| CONSTRUCTS |  |  |  |  |
| YUU | Tensile | ** | ** | ** |
| YUQ, Sample One | Tensile | 1.26 | 0.51 | 7 |
| YUQ, Sample Two | Tensile | 3.02 | 1.05 | 7 |
| Pooled Data From Above YUQ Samples One and Two | Tensile | 2.14 | 1.21 | 14 |
| YAU | Tensile | 2.76 | 0.49 | 7 |
| YAQ | Tensile | 7.04 | 0.56 | 7 |

**Meshes dissolved after contact with lyophilizing solvent. Construct reinforced with unannealed, unquenched yarn mesh could not be fabricated. One would then expect the values here to correspond to those generated by the "Foam" alone.

Example 6

Mechanical Properties of Monofilament Mesh Constructs

This example describes the testing of mechanical properties of the reinforced meshes made in Examples 3 and 4. The components of the constructs were tested as controls. It is noted that the mesh controls were scoured according to the procedure outlined in Example 1.

Peak loads of constructs described in Examples 3 and 4 were measured using an Instron machine (Model 4501, Instron, Inc., Canton, Mass.), outfitted with a 20 lb. load cell. The specimens were cut (40 mm×9.9 mm) using a die cutter (with the exception of the mesh controls that were cut with scissors), the thickness of each specimen was measured prior to testing. Seven specimens of each control and construct type were measured. Pneumatic grips with rubber coated faces were used grip the samples such that a 20 mm gauge length, the length of the construct between the grips, was present at the start of the experiment. The grip pressure was set at 50 psi. The cross-head speed was one inch per minute.

Table 3 shows the peak loads for the controls and constructs formed with monofilament meshes (diameter=5 mil). The table shows that without annealing and quenching steps (MUU), the peak load of a construct was unable to be measured due to the fact that the monofilament mesh dissolved in the processing solvent. When a quenching step is added, the peak load of a monofilament mesh construct is measured to be 1.6 lb. The mechanical properties are further improved when the reinforcing monofilament mesh is pre-annealed and quenched (MAQ=4.8 lb). The addition of the annealing step without the quenching step (MAU) also results in improved properties (1.8 lb).

TABLE 3

Tensile Test Results

|  | Peak load (lb) | STD (lb) | N |
|---|---|---|---|
| CONTROL |  |  |  |
| Foam | 0.92 | 0.26 | 7 |
| Monofilament Mesh, Scoured | 3.21 | 0.89 | 7 |
| Monofilament Mesh CONSTRUCTS | 4.07 | 2.28 | 3 |
| MUU | ** | ** | ** |
| MUQ | 1.62 | 0.34 | 7 |
| MAU | 1.83 | 0.24 | 7 |
| MAQ | 4.77 | 0.43 | 7 |

**Meshes dissolved after contact with lyophilizing solvent. Construct reinforced with unannealed, unquenched monofilament mesh could not be fabricated. One would then expect the values here to correspond to those generated by the "Foam" alone.

Example 7

Surgical Procedure

A patient is prepared for surgery in a conventional manner using conventional surgical preparatory procedures. The patient has a soft tissue injury involving a tear in the supraspinatus tendon of the rotator cuff. In an older patient, the tendon is thin and degenerate and therefore the traditional methods for reapproximation of the tendon edge to the insertion site on the humerus cannot be performed. Since the tendon is degenerate, the strength of the fixation will not allow for proper rehabilitation. The patient is anesthetized in a conventional manner and the operation is performed arthroscopically.

In a first surgical procedure, the implant of the present invention is used to augment or reinforce the fixation. The bioabsorbable implant is cut to size such that the width of the implant is the same or slightly smaller than the width of the native supraspinatus tendon. The length of the implant is cut such that it spans the degenerate portion of the tendon as well as some of the healthy portion of the tendon. The implant is then sutured on top of the degenerate and healthy portion of the tendon. The medial wall of the greater tuberosity is then prepared with 3-5 drill holes. Suture anchors such as Bio-Knotless brand suture anchors (Mitek, Norwood, Mass.) threaded with No. 1 Ethibond are inserted into the holes. The sutures on the anchors pass through both the tendon and the implant to reattach the implant-reinforced supraspinatus tendon construct to the original insertion site of the tendon.

In an additional surgical procedure, an implant of the present invention is used as an extender to the tendon. This is necessary when there is too much degeneration in the tendon or if there is retraction in the tendon. One end of the implant is sutured to the healthy portion of the supraspinatus tendon with nonresorbable Ethibond brand sutures (Ethicon, Somerville, N.J.). The other end is attached to the medial wall of the greater tuberosity using suture anchors. The implant is cut to match the width of the tendon and to properly fill the gap between the tendon and its insertion site. In this case, the implant will serve as a bridge between the tendon and the attachment site. The surgical site is closed using conventional surgical techniques and the patient is removed from anesthesia and sent to a recovery room.

Example 8

Preparation of Poly(Lactide-Co-Glycolide) Monofilament Fiber

A 95/5 poly(lactide-co-glycolide) resin was extruded using a JJ Jenkins extruder with a 1" diameter three-zone barrel having an VD of 24:1. A 3:1 compression screw was used; extrusion temperatures ranged from 190 to 240° C. and the polymer melt temperature was 220° C. The extrudate was quenched using a 20° C. water bath. The extrudate was then drawn 6× using godet temperatures of 65 to 75° C. and a single 6' orientation oven set at 95° C. The resulting monofilament had a diameter of 5.0 mils, a tensile strength of 93.8 kpsi, an elongation-to-break of 27.9%, and a Young's Modulus of 1054 kpsi.

A portion of this fiber sample was then in-line annealed at 20 feet per minute at 146° C. through two 6' hot air ovens (12' total). Physical properties of the resulting annealed monofilament had a diameter of 4.96 mils, a tensile strength of 69.8 kpsi, an elongation-to-break of 43%, and a Young's Modulus of 1102 kpsi. This fiber was then coated with poly(p-dioxanone) resin to achieve different levels of coating thickness.

Example 9

Coating Of Fiber With Poly(p-Dioxanone) Resin

Melt coating of a sheath onto pre-existing fiber was done. A Randcastle extruder was used for the melting coating of the fiber of Example 8 with poly(p-dioxanone). The extruder had a ⅝" diameter barrel and a L/D of 20.8:1 (13" barrel). It was a standard three-zone barrel; a 3:1 compression screw was used. The extrusions temperatures were run in a reverse profile ramping from 132 to 143° C. then back down to 129° C. The melt temperature was 146° C. The poly(p-dioxanone) coating was air-cooled. Godet speeds ranged from 30 to about 50 feet per minute to achieve the thin coating. The slower the speed, the thicker the coating.

Coating thicknesses of approximately 1.0, 1.75, 2.375, 4.0 mils were achieved. The final overall diameters of the coated fibers were 7.0, 8.5, 10.0, and 13.0 mils respectively.

Example 10

Poly(p-Dioxanone) Coating Adherence to 95/5 Poly(Lactide-co-Glycolide) Fiber (Knot Test)

The purpose of the following experiment was to prove the integrity of 95/5 poly(lactide-co-glycolide) fibers coated with poly(p-dioxanone).

Figure 10:
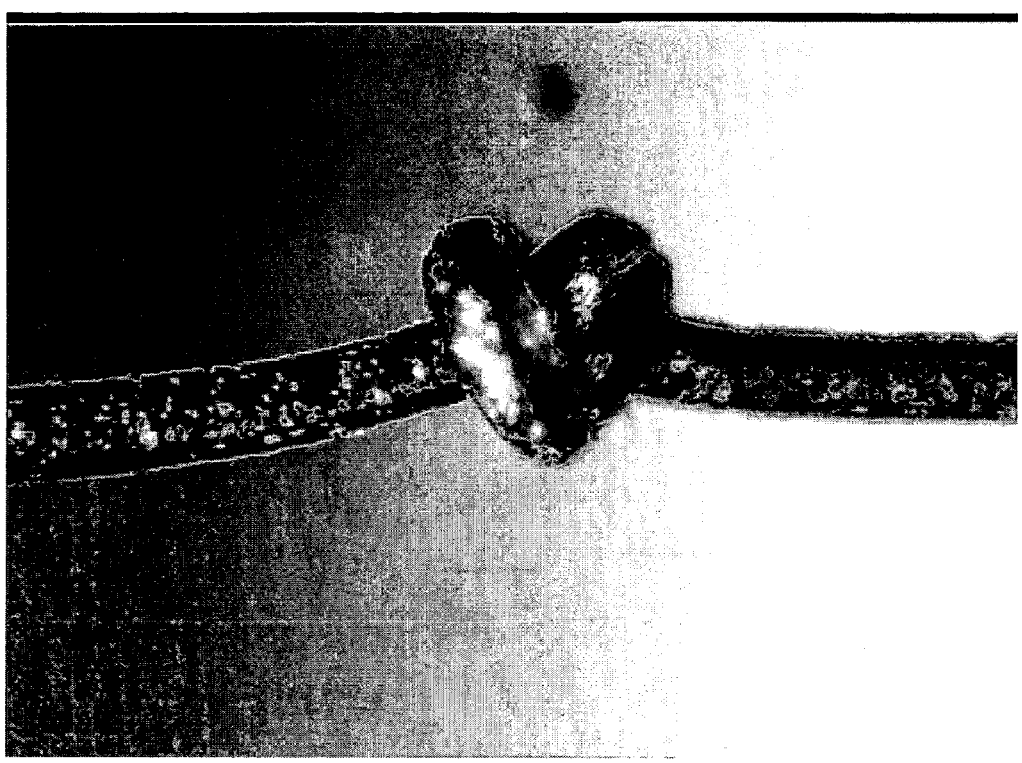
FIG. 10($a$) is a photographic depiction of poly(p-dioxanone) coated, 5 mil 95/5 poly(lactide-co-glycolide) fiber tied into a knot, the coating thickness is 1.0 mil.

In order to test the initial integrity of the poly(p-dioxanone) coating, the fibers of 95/5 poly (lactide-co-glycolide) coated with varying thicknesses of poly(p-dioxanone) coating of Example 9 were tied into knots as shown in FIG. 10 to determine the tendency for the coating to detach from the core fiber under this stress. For all coating thicknesses, the knots were capable of being tied tight without any sign of detachment of the coating from the core.

Example 11

Poly(p-Dioxanone) Coating Integrity (Washer Test)

Figure 11:
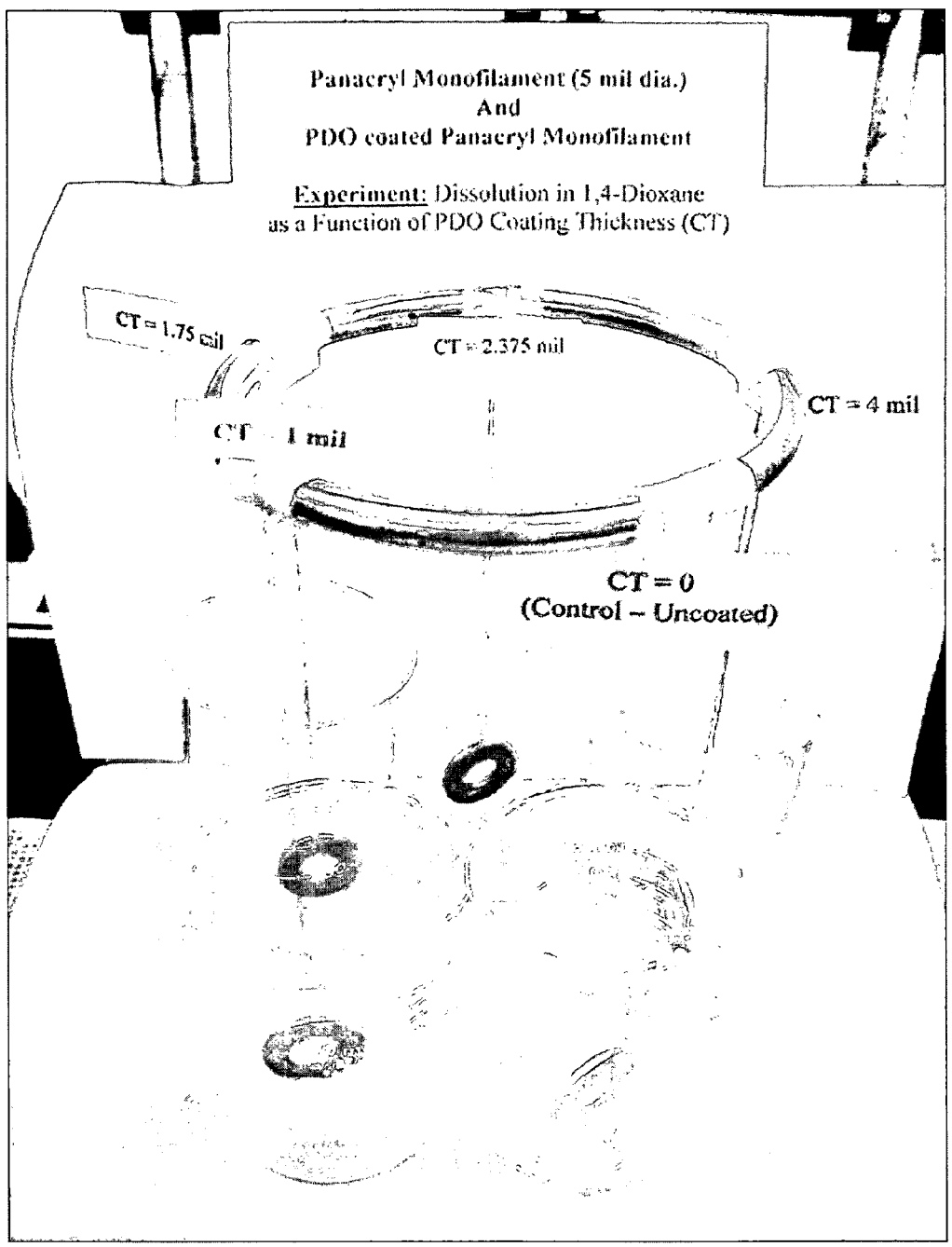
FIG. 11 is a photograph illustrating the setup used to test poly(p-dioxanone) coating integrity in which the ends of the fiber were not submerged in the solvent before testing.

In order to verify coating efficacy, the uncoated fiber of 95/5 poly(lactide-co-glycolide) of Example 8 and the fibers of 95/5 poly(lactide-co-glycolide) coated with varying thicknesses of poly(p-dioxanone) coating of Example 9 were cut into lengths and placed in 1,4-dioxane without allowing the ends of the fiber to contact the solvent. A washer was threaded onto the lengths of fiber and used to weigh down the fiber lengths in the solvent while both ends were kept out and attached to a cantilever above the beaker of solvent as shown in FIG. 11. The pure, uncoated 95/5 poly(lactide-co-glycolide) dissolved within 40 seconds and the washer threaded onto this fiber fell to the bottom of the beaker. The remaining coated fibers were left in the solvent for 2 days after which time, the washer was observed to remain dangling, indicating that the poly(p-dioxanone) coatings protected the fiber from dissolution.

Example 12

Effect of De-Protected Ends of Poly(p-Dioxanone) Coating on 95/5 Poly-(Lactide-Co-Glycolide) Fiber (Submersion Test)

Figure 12:
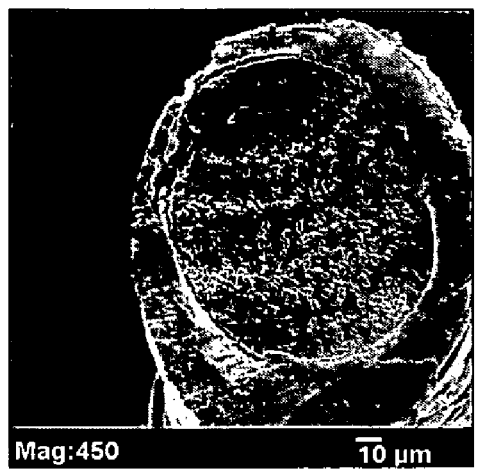
FIG. 12 is a micrograph of a cross-section of a short segment of poly(p-dioxanone) coated (coating thickness 1.0 mil) 95/5 poly(lactide-co-glycolide) 5.0 mil fiber for which the ends were exposed during submersion of the fiber segment in 1,4-dioxane for 30 hours.
Figure 13:
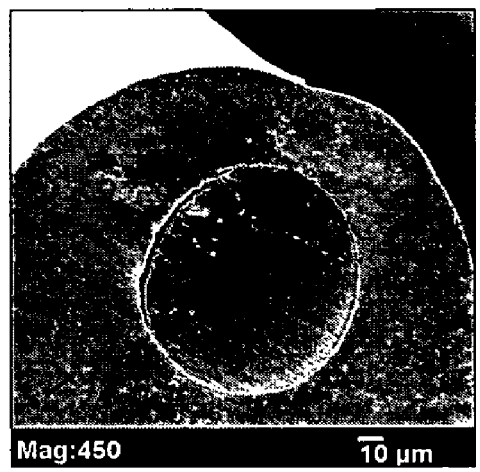
FIG. 13 is a micrograph of a cross-section of a short segment of poly(p-dioxanone) coated (coating thickness 4.0 mil) 95/5 poly(lactide-co-glycolide) 5.0 mil fiber for which the ends were exposed during submersion of the fiber segment in 1,4-dioxane for 30 hours.

The fibers of 95/5 poly(lactide-co-glycolide) coated with varying thicknesses of poly(p-dioxanone) coating of Example 8 were cut into pieces and placed in dishes filled with 1,4-dioxane. Half inch to one inch segments of coated fiber from each diameter size were cut and placed in dishes filled with 1,4-dioxane. Segments were taken out of the 1,4-dioxane after 8 and 30 hours. Residence time in 1,4-dioxane did not result in complete coring of the fiber leaving behind a poly(p-dioxanone) small diameter tube. In fact, a 95/5 poly(lactide-co-glycolide) fiber core was visible by SEM in all size groups at both time points as shown in FIGS. 12 and 13. The presence of the 95/5 poly(lactide-co-glycolide) fiber core indicates the relative stability of coated fiber with de-protected ends when placed in 1,4-dioxane during processing residence times that would be orders of magnitude smaller.

Example 13

Tensile Testing of Polydioxanone-Coated 95/5 Poly(Lactide Co-Glycolide) Fibers.

Four 95/5 poly(lactide co-glycolide) fibers were tested using an Instron model 4501 (Canton, Mass.). Seven samples of each group were tested. Grip pressure was set at fifty psi. A 20 lb load cell was used. The cross head speed was 2 inch/minute. Rubber faced grips were used. The gage length, distance between the grips, was 2.0 in.

| Groups were identified as follows: |  |
|---|---|
| Group #1: | Uncoated 95/5 poly(lactide co-glycolide) fiber (5 mil unannealed) |
| Group #2: | Uncoated 95/5 poly(lactide co-glycolide) fiber (5 mil in line annealed at 146° C. at 20 feet per minute) |
| Group #3: | Poly(p-dioxanone) coated 95/5 poly(lactide co-glycolide) fiber (7 mil in-line annealed at 146° C. at 20 feet per minute) |
| Group #4: | Poly(p-dioxanone) coated 95/5 poly(lactide co-glycolide) fiber (13 mil in-line annealed at 146° C. at 20 feet per minute). |

Sets of samples were submerged in 1,4-dioxane for 3 minutes, and the results are shown in Table 4.

TABLE 4

| Group | Peak load before (lb) (mean value/stand. deviation) | Peak load after (lb)* (mean value/stand. deviation) |
|---|---|---|
| 1 | 1.58 +/− 0.29 | N/A** |
| 2 | 1.43 +/− 0.04 | N/A*** |
| 3 | 1.59 +/− 0.04 | 1.11 +/− 0.06 |
| 4 | 1.89 +/− 0.11 | 1.80 +/− 0.07 |

*Samples were soaked in 1,4-dioxane solvent for 3 minutes before testing.
**Samples were dissolved and could not be tested.
***Samples of this group were too weak to handle and could not be tested.

As shown in Table 4, the uncoated, unannealed and annealed fibers dissolved after exposure to dioxane. The dissolution of the uncoated, unannealed fiber was expected based on the experiments with unannealed, unquenched monofilament mesh as cited in Example 6. The dissolution of the uncoated, annealed fiber was somewhat unexpected due to the dissolution resistance in dioxane imparted to unquenched monofilament mesh upon annealing as cited in Example 6. However, the annealed unquenched monofilament mesh had been annealed for 3 hours at 120° C. while the monofilament fiber in this example was annealed for only 36 seconds at 146° C. While the temperature was elevated, the duration was not sufficient to render the fiber resistant to dissolution in dioxane.

While annealing conditions were not sufficient, the application of poly(p-dioxanone) coating to the fiber was successful in rendering the fiber resistant to dissolution in dioxane. The coated fiber maintained strength after immersion in the solvent, both at larger (13 mil) and smaller (7 mil) diameter. Reinforcements based on monofilament fiber, especially larger diameter fiber, may be even more advantageous in certain circumstances.

The reinforced implants of the present invention have numerous advantages. In the past, traditional repair techniques have had failures due to inadequate fixation of the tendon to bone or lack of tendon-to-bone healing. A slow-resorbing implant that has good mechanical strength will bear load at initial time points and allow for good fixation strength at the tendon-bone interface. The use of the bioabsorbable implants of the present invention that support cell migration and growth will allow for the cells from neighboring tissue to migrate into the implant site and produce matrix that is similar to that of native tissue. When the implants of the present invention are used to augment the fixation, greater area of contact exists between the tendon-implant and bone and therefore may enhance the healing response at the interface. When an implant of the present invention is used as an extender, the implant will support the migration of cells from the native tendon and bone and allow for biological healing of the tendon-tendon and tendon-bone interfaces.

The process of manufacture provided herewithin allows the fabrication of at least partially absorbable surgical devices that have great utility in those applications require the retention of mechanical properties for relatively extended periods of time in vivo. Although polylactide and its copolymers are well known to retain mechanical integrity for long periods of time, their fibers present a problem when exposed to many lyophilizing solvents, such as p-dioxane. The fibers tend to loss their strength completely preventing them from being used as reinforcing agents. It will be recognized that the process of the present invention allows the use of reinforcing fibers rich in polylactide. This is accomplished by treating the reinforcing agents with a polymeric coating. The coating can be applied by various means; of particular utility is melt coating of a preformed fiber.

Although this invention has been shown and described with respect to detailed embodiments thereof, it will be understood by those skilled in the art that various changes in form and detail thereof may be made without departing from the spirit and scope of the claimed invention.

We claim:

1. A method of repairing damaged tissue, comprising: providing a biocompatible tissue implant comprising: a biocompatible polymeric foam, said foam soluble in a lyophilizing solvent; a biocompatible polymeric reinforcement member, said reinforcement member soluble in the lyophilizing solvent; and, a polymeric coating having a thickness applied to the reinforcement member, said coating comprising a coating polymer, wherein said coating polymer is substantially insoluble in said lyophilizing solvent; and, placing the implant in a desired position at a site relative to a tissue injury.

2. The method of claim 1, wherein the implant is placed within a lesion that constitutes the tissue injury.

3. The method of claim 2, wherein the implant is over the lesion.

4. The method of claim 2, wherein the implant is of a size and shape such that it matches a geometry and dimension of the lesion.

5. The method of claim 2, wherein the implant is placed within the lesion in an interference fit.

6. The method of claim 1, wherein the implant is placed adjacent to a lesion that constitutes tear such that the implant reinforces the tissue.

7. The method of claim 1, wherein the implant is wrapped around tissue having a lesion.

8. The method of claim 1, wherein the foamed polymer and the polymeric reinforcement member comprise bioabsorbable polymers.

9. The method of claim 1, wherein the implant is affixed to the site by suturing.

10. The method of claim 1, wherein the implant is affixed to the site by stapling.

11. The method of claim 1, wherein the implant is affixed to the site by using a glue.

12. The method of claim 1, wherein the implant is affixed to the site by using a device selected from the group consisting of suture anchors, tissue tacks, darts, screws, arrows, and combinations thereof.

13. The method of claim 11, wherein the glue is selected from the group consisting of fibrin glues, fibrin clots, platelet rich plasma, platelet poor plasma, blood clots, biologically compatible adhesives, and combinations thereof.

14. The method of claim 1 wherein the tissue comprises soft tissue.

15. The method of claim 1 wherein the coating is bioabsorbable.

16. The method of claim 15 wherein the coating comprises a polymer selected from the group consisting of polydioxanone, and its copolymers with L(−)-lactide, D(+)-lactide, meso-lactide, trimethylene carbonate, epsilon-caprolactone, or glycolide, or combinations thereof, with the provision that polymerized dioxanone is at least 50 weight percent.

17. The method of claim 15, wherein the coating comprises poly(p-dioxanone).

18. The method of claim 1, wherein the thickness of the coating is greater than about 1.0 mil.

19. The method of claim 1, wherein the lyophilizing solvent is selected from the group consisting of p(dioxane) and trioxane.

20. The method of claim 19, wherein the lyophilizing solvent comprises p(dioxane).

* * * * *